(12) United States Patent
Broyles et al.

(10) Patent No.: US 8,328,553 B2
(45) Date of Patent: Dec. 11, 2012

(54) DEVICE FOR DISPENSING MATERIAL

(75) Inventors: Bruce R. Broyles, Oakdale, MN (US);
Marc Peuker, Schondorf (DE);
Sebastian Guggenmos, Peissenberg (DE); Andreas J. Boehm, Reichling (DE); Hubert Schloegl, Landsberg (DE); Michael Knee, Peissenberg (DE); Werner Fichtl, Geltendorf/Kallenberg (DE); John W. Dubbe, Stranberg (DE); Arno Hohmann, Munich (DE); Darin J. Meyertholen, Woodbury, MN (US);
Dean K. Reidt, Cottage Grove, MN (US); Steven J. Maxa, Burnsville, MN (US); Urs Mahnel, Bad Tölz (DE)

(73) Assignee: 3M Innovative Properties Company, Saint Paul, MN (US)

( * ) Notice: Subject to any disclaimer, the term of this patent is extended or adjusted under 35 U.S.C. 154(b) by 646 days.

(21) Appl. No.: 12/281,996

(22) PCT Filed: Mar. 9, 2007

(86) PCT No.: PCT/US2007/063635
§ 371 (c)(1),
(2), (4) Date: May 8, 2009

(87) PCT Pub. No.: WO2007/104037
PCT Pub. Date: Sep. 13, 2007

(65) Prior Publication Data
US 2009/0298010 A1    Dec. 3, 2009

Related U.S. Application Data

(60) Provisional application No. 60/780,536, filed on Mar. 9, 2006.

(51) Int. Cl.
*A61C 5/04*    (2006.01)
*A61C 17/00*    (2006.01)
*A61C 17/02*    (2006.01)

(52) U.S. Cl. .............................. 433/90; 433/80; 433/89

(58) Field of Classification Search .................. 433/80, 433/89–90, 82, 97, 99, 100, 103, 108, 109, 433/114, 115, 120, 126; 206/219–222, 452, 206/453; 403/34–39, 320; 285/260–268; 215/312; 604/246, 248, 256; 251/192; 222/145.4, 222/531, 532, 534
See application file for complete search history.

(56) References Cited

U.S. PATENT DOCUMENTS
2,032,776 A * 3/1936 Van Ness .................... 222/541.6
(Continued)

FOREIGN PATENT DOCUMENTS
CH    669 164    1/1989
(Continued)

*Primary Examiner* — Yogesh Patel
(74) *Attorney, Agent, or Firm* — Peter L. Olson; Dean M. Harts; Qiang Han

(57) ABSTRACT

A capsule for storing and dispensing dental material. The capsule comprises a cartridge for the dental material, and a nozzle. The nozzle being pivotable with respect to the cartridge between a first position in which the capsule is closed for storage and a second position in which the capsule is opened for dispensing the dental material. One of the nozzle and the cartridge comprises a bearing member and the other one of the nozzle and the cartridge comprises a bearing shell, wherein the bearing member and bearing shell form a pivot. Upon pivoting the nozzle from the first to the second position, the seal between the bearing member and the bearing shell is improved.

14 Claims, 13 Drawing Sheets

U.S. PATENT DOCUMENTS

| | | | | |
|---|---|---|---|---|
| 3,089,626 | A | 5/1963 | Kubiliunas | 222/484 |
| 3,251,516 | A | 5/1966 | Thomas | 222/536 |
| 3,323,682 | A | 6/1967 | Creighton et al. | 222/94 |
| 3,863,818 | A | 2/1975 | Hazard | 222/531 |
| 4,121,739 | A | 10/1978 | Devaney et al. | 222/137 |
| 4,471,888 | A | 9/1984 | Herb et al. | 222/137 |
| 4,538,920 | A | 9/1985 | Drake | 366/177 |
| 4,674,661 | A | 6/1987 | Herold | 222/386 |
| 4,687,663 | A | 8/1987 | Schaeffer | 424/52 |
| 4,735,509 | A | 4/1988 | Rausch | |
| 4,801,008 | A | 1/1989 | Rich | 206/219 |
| 4,823,946 | A * | 4/1989 | Stoeffler et al. | 206/221 |
| 4,995,540 | A | 2/1991 | Colin et al. | |
| 5,033,650 | A | 7/1991 | Colin et al. | |
| 5,065,906 | A | 11/1991 | Maeder | |
| RE33,801 | E * | 1/1992 | Green | 222/82 |
| 5,082,147 | A | 1/1992 | Jacobs | 222/137 |
| 5,127,548 | A | 7/1992 | Brunet et al. | |
| 5,137,181 | A | 8/1992 | Keller | 222/134 |
| 5,242,082 | A | 9/1993 | Giannuzzi | |
| 5,249,709 | A | 10/1993 | Duckworth et al. | 222/137 |
| 5,333,760 | A | 8/1994 | Simmen | 222/137 |
| 5,370,221 | A | 12/1994 | Magnusson et al. | |
| 5,535,922 | A | 7/1996 | Maziarz | 222/137 |
| 5,647,510 | A | 7/1997 | Keller | |
| 5,743,436 | A | 4/1998 | Wilcox et al. | 222/137 |
| 5,897,028 | A | 4/1999 | Sauer | |
| 6,047,861 | A | 4/2000 | Vidal et al. | |
| 6,048,201 | A | 4/2000 | Zwingenberger | |
| 6,065,643 | A | 5/2000 | Harvey et al. | 222/94 |
| 6,352,177 | B1 | 3/2002 | Bublewitz et al. | |
| 6,375,460 | B1 | 4/2002 | Plaumann | 433/80 |
| 6,386,872 | B1 | 5/2002 | Mukasa et al. | 433/90 |
| 6,409,972 | B1 | 6/2002 | Chan | |
| 6,454,129 | B1 | 9/2002 | Green | |
| 6,464,112 | B2 | 10/2002 | Summons et al. | |
| 6,547,101 | B1 | 4/2003 | Sogaro | |
| 6,681,957 | B1 | 1/2004 | Green | |
| 6,843,652 | B2 | 1/2005 | Xie et al. | |
| 7,882,983 | B2 | 2/2011 | Reidt | |
| 2002/0023892 | A1 * | 2/2002 | Savitz et al. | 215/312 |
| 2003/0111490 | A1 | 6/2003 | Pierson | 222/145 |
| 2003/0147688 | A1 * | 8/2003 | Hathaway | 403/90 |
| 2004/0104249 | A1 | 6/2004 | Horth | |
| 2004/0152041 | A1 * | 8/2004 | Metzbower | 433/90 |
| 2005/0130099 | A1 * | 6/2005 | Besek et al. | 433/80 |
| 2006/0273109 | A1 * | 12/2006 | Keller | 222/145.5 |

FOREIGN PATENT DOCUMENTS

| | | |
|---|---|---|
| CN | 2397066 | 9/2000 |
| DE | 2 219 009 | 10/1973 |
| DE | 39 13 409 | 10/1990 |
| DE | 90 16 568.3 | 5/1992 |
| DE | 92 06 892 | 1/1993 |
| DE | 197 08 548 | 9/1998 |
| DE | 696 17 260 | 7/2002 |
| DE | 101 33 075 | 1/2003 |
| DE | 101 51 104 | 4/2003 |
| EP | 00 931 85 | 5/1982 |
| EP | 0 157 121 | 10/1985 |
| EP | 0 249 701 | 12/1987 |
| EP | 0 783 872 | 7/1997 |
| EP | 0 831 034 | 8/1997 |
| EP | 1 430 959 | 6/2004 |
| EP | 1 544 123 | 6/2005 |
| FR | 1 493 380 | 8/1967 |
| JP | S62-65969 | 4/1987 |
| JP | S61-99566 | 7/1994 |
| JP | 2002-145360 | 11/2000 |
| WO | WO 95/22941 | 8/1995 |
| WO | WO 96/15705 | 5/1996 |
| WO | WO 97/21394 | 6/1997 |
| WO | WO 01/44065 | 6/2001 |
| WO | WO 02/094683 | 11/2002 |
| WO | WO 2005/016783 | 2/2005 |

* cited by examiner

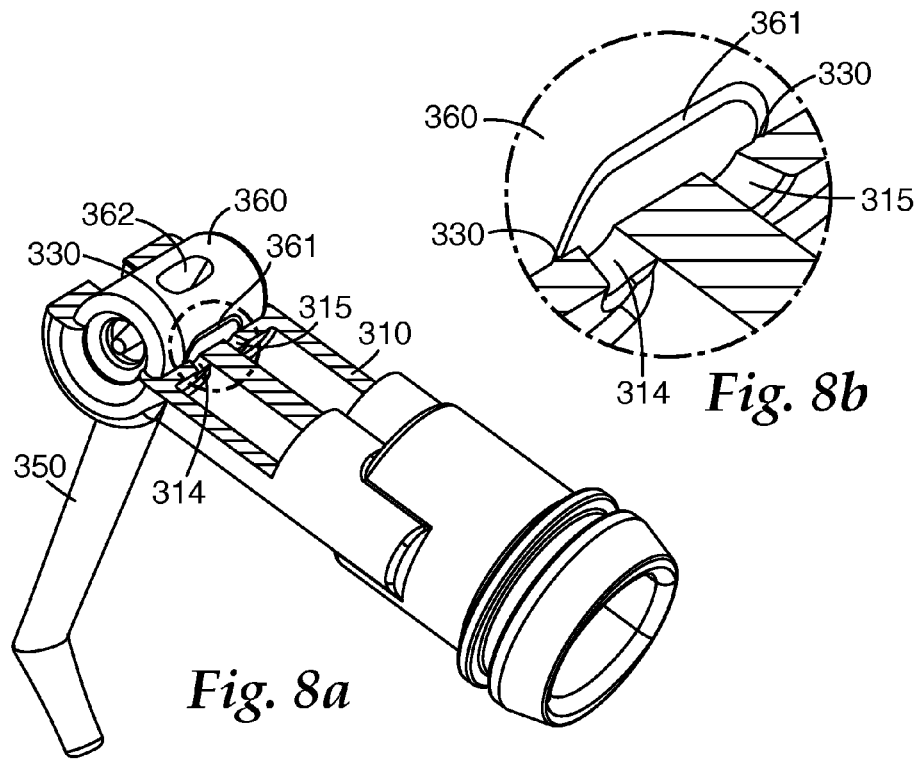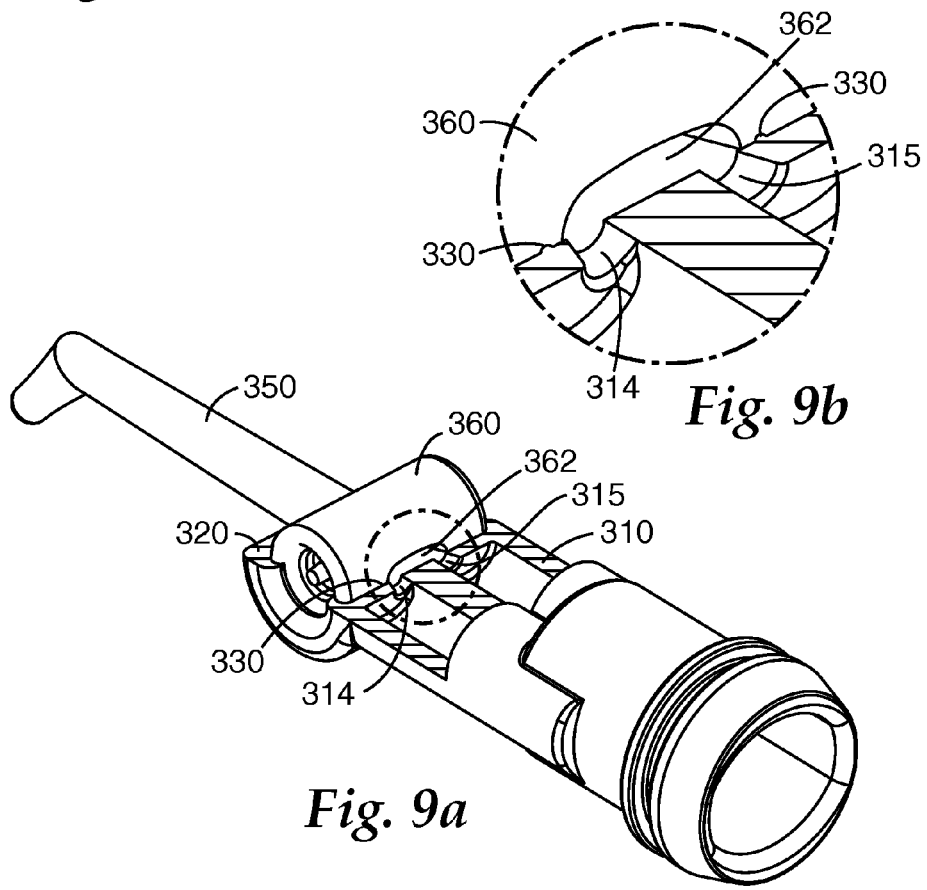

DEVICE FOR DISPENSING MATERIAL

CROSS REFERENCE TO RELATED APPLICATIONS

This application is a national stage filing under 35 U.S.C. 371 of PCT/US2007/063635, filed Mar. 9, 2007, which claims priority to U.S. Provisional Application No. 60/780,536, filed Mar. 9, 2006, the disclosure of which is incorporated by reference in their entirety herein.

FIELD OF THE INVENTION

The present invention relates to capsules for storing and dispensing material, such as a liquid or paste. In particular, the invention relates to a capsule for two or more components of a material which are to be mixed together. The material can be a dental material, for example an impression material, a temporary restoration material or a filling material.

BACKGROUND

In dentistry, various capsules are known for the preparation and/or delivery of dental materials consisting of one component or of two or more components which are to be mixed together. There are single-component capsules, powder/liquid capsules, and paste/paste capsules.

A compule is a capsule having a cannula, a single chamber containing a one-component material with an opening at the front into the cannula, and a piston which sits in the rear of the chamber. Such compules can contain, for example, the universal filler material Filtek™ Supreme and the universal composite Filtek™ Z250 available from 3M ESPE. For use, the capsule has to be inserted into an applicator which, for example, is available from 3M ESPE as Capsule dispenser under article number 5706 SD, or from Centrix under the designation Mark IIIp™. These known applicators each have a body with a handgrip, a holder for receiving the compule in a removable manner, a plunger, and a drive mechanism for the plunger. When the capsule sits in the holder and the drive mechanism is actuated by hand, the drive mechanism pushes the plunger into the chamber from the rear, so that the plunger initially bears on the piston and pushes it forwards. The material is dispensed from the chamber through the cannula due to the advancement of the piston.

The liquid/powder capsules contain a liquid component and a powder component which have to be kept separate from one another until the time of use. Such liquid/powder capsules are, for example, available under the names Aplicap™ and Maxicap™ from 3M ESPE. These capsules contain, for example, the two components to be mixed together. The components may be those related to filler materials such as, for example, the glass ionomer filler material Ketac™ Molar, or the light-cured glass ionomer filler material Photac™ Fil Quick, or the silver-reinforced glass ionomer filler material Ketac™ Silver Molar, or luting cements such as, for example, the self-adhesive universal composite luting cement RelyX™ Unicem or the adhesive composite luting cement Compolute™ or the glass ionomer luting cement Keta™ Cem.

These known capsules have a cannula, a large mixing chamber which contains the powder and opens at the front into the cannula, a piston which sits at the rear in the mixing chamber, and a foil pouch which contains the liquid and covers a hole in the shell or outer wall of the chamber. To use the capsule, it is first activated by applying pressure in a suitable way to the foil pouch, so that the latter tears near the hole and the liquid is forced into the mixing chamber. The mixing chamber is larger than the combined volume of the two components, so that these can be mixed together by vigorous agitation, for example using the capsule mixer devices RotoMixT™ or CapMixT™ from 3M ESPE. The capsule is then inserted into a suitable applicator that dispenses the mixed material.

The paste/paste capsules contain two pasty components which have to be kept separate from one another until the time of use. Such a paste/paste capsule is known from, for example, WO 2005/016783. The capsule 1, as shown in FIG. 1, comprises a cartridge 2, a first component chamber 4 for containing a first component, and a second component chamber 5 for containing a second component. The two component chambers 4, 5 open into outlets. The capsule 1 also comprises a plunger 70 with a first piston 6 and a second piston 7 being adapted to press the two components out of the component chambers 4, 5 respectively, when the plunger is pushed forward. A common partition wall 14 separates the two component chambers 4, 5 from one another. The nozzle 10, in which a static mixer 11 is accommodated, is pivotably joined with the cartridge 1. The nozzle 10 comprises a bearing member 12 which is arranged in bearing shell 13 of cartridge 1. The nozzle 10, in a first position (not shown), closes off the outlets of the cartridge 1 and, in a second position (shown in FIG. 1), connects the outlets to a passageway of the nozzle 1. The chambers 4, 5 contain the two pasty components which, upon pushing the plunger forward via actuation of an applicator, are expelled from the chambers 4, 5 into the nozzle 10. As they flow through the nozzle 10, the two components become mixed by the static mixer 11 and finally dispensed as a ready-mixed material from the front end of the nozzle 10.

SUMMARY OF THE INVENTION

According to a first aspect, the invention provides a capsule for storing and dispensing dental material. The capsule comprises a cartridge for the dental material, and a nozzle. The nozzle is pivotable with respect to the cartridge between a first position (see FIG. 2) in which the capsule is closed for storage, and a second position (see FIG. 3) in which the capsule is opened for dispensing the dental material. One of the nozzle and the cartridge comprises a bearing member and the other one of the nozzle and the cartridge comprises a bearing shell. The bearing member and bearing shell form a pivot. Preferably the nozzle comprises the bearing member and the cartridge comprises the bearing shell. The bearing member is preferably joined with the bearing shell such that upon pivoting the nozzle from the first to the second position, the seal between the bearing member and the bearing shell is improved. According to one embodiment of the invention, the seal is improved due to an increase in the pressure between at least a part of the surface of the bearing shell and a corresponding opposite part of the surface of the bearing member in the second position of the nozzle is higher than in the first position.

The improved sealing properties according to the present invention are not considered to be a random or normal effect, for example as a result of an difference in manufacturing tolerances between parts, but rather to be the result of structural features intentionally designed to provide an improved seal (for example due to an increase in pressure beyond pressure changes caused by random or normal manufacturing effects) as mentioned.

The bearing member is preferably sized and shaped such that it matches the size and shape of the bearing shell in the first position of the nozzle, but mismatches or differs from the size and shape of the bearing shell in the second position of the nozzle. Thus, there may be essentially uniform pressure and no gaps between the bearing member and the bearing shell while in the first position, but there may be non-uniform pressure and in some cases gaps between the bearing member and the bearing shell while in the second position.

The capsule of the invention comprises a chamber opening into an outlet. It is preferred that the cartridge comprises a first chamber for containing a first material component, and a second chamber for containing a second material component. Each of the chambers opens into an outlet. More preferably the first chamber opens into a first outlet and the second chamber opens into a second outlet. In another embodiment both chambers open into the same outlet.

The capsule can also comprise a plunger for dispensing material from the cartridge via the outlet(s) and through the nozzle.

The nozzle preferably comprises a cannula which protrudes from the bearing member of the nozzle. The cannula preferably is an elongated part comprising a dispensing tip at its free end. The tip is preferably inclined with respect to the longitudinal axis of the cannula. In an alternative embodiment, the cannula incorporates the dispensing tip, e.g. is shaped such that the free end provides the function of a dispensing tip. The cannula preferably is straight or curved and preferably decreases in its outer diameter from the bearing member toward the free end. The nozzle further comprises a passageway extending from an inlet in the bearing member to an orifice in the cannula or tip, wherein the passageway preferably has a smaller cross-section at the orifice than the cross-section at the inlet. The passageway preferably comprises an inlet section adjacent to the inlet, an outlet section adjacent to the orifice and a mixing channel extending between the inlet and outlet sections. The inlet section is preferably generally funneled and passes into the mixing channel. The mixing channel preferably has a substantially circular cross-section of a substantially constant diameter over its length and the outlet section comprises a narrowed or constricted cross-section relative to the diameter of the mixing channel. Preferably a step is formed at the junction of the mixing channel and the outlet section. In an optional embodiment the mixing channel comprises a rectangular cross-section, e.g. for accommodation of a rectangular static mixer, such as a Quadro™ Mixer available from the Sulzer Chemtech Ltd. Company of Switzerland. The mixing channel may also be tapered and/or comprise at least one constricted area.

The first position of the nozzle is preferably a storage position in which the nozzle closes off the outlet(s) of the cartridge, and the second position is preferably an operative position in which the passageway of the nozzle is in fluid communication with the outlet(s) of the cartridge. The pivot axis of the bearing is preferably transverse to the longitudinal axis of the cartridge. Furthermore, the pivot axis of the bearing is preferably transverse to the longitudinal axis of the nozzle. In case the nozzle comprises a curved cannula, the longitudinal axis of the nozzle is preferably defined by a tangent of the curve through a point of the pivot axis.

According to a preferred embodiment, the shape of the bearing member and the shape of the bearing shell are different from each other in the second position of the nozzle to create a compressive force between the bearing member and the bearing shell so that the one is pressed against the other to improve the seal therebetween. Preferably, the shape of the bearing member and the shape of the bearing shell generally match in the first position of the nozzle, but generally differ from each other in the second position of the nozzle. More preferably, the cross-sectional shape of the bearing member in a plane perpendicular to its rotation axis is such that it generally matches the cross-sectional shape of the bearing shell in this plane in the first position of the nozzle but generally differs from the cross-sectional shape of the bearing shell in the second position of the nozzle. Preferably, the bearing member comprises a non-circular cross-sectional shape in a plane perpendicular to its rotation axis. For example, the bearing member may have an elliptical cross-section. In the first position of the nozzle, the short axis of the ellipse is preferably aligned with the longitudinal axis of the cartridge. Alternatively, the bearing member comprises a cross-section that has one or more curved sections, but is not circular.

According to an alternative embodiment, the bearing member, for example of the nozzle, comprises a structured outer surface, and the bearing shell, for example of the cartridge, comprises a structured inner surface. The structure of the outer surface of the bearing member generally matches the structure of the inner surface of the bearing shell in the first position of the nozzle, but generally mismatches or differs from the structure of the inner surface of the bearing shell in the second position of the nozzle. Preferably, the structure of the outer surface of the bearing member is a recessed structure and the structure of the inner surface of the bearing shell is a corresponding raised structure. More preferably, the structure of the outer surface of the bearing member is a recessed area, such as a groove, and the structure of the inner surface of the bearing shell is a corresponding raised area, such as a bulge or a raised ridge. The groove preferably continues along a closed curve or path on the outer surface of the bearing member and the raised ridge corresponds to it. The recessed structure may also be a completely recessed area, compared to a groove surrounding a non-recessed area. The recessed structure may also be a groove surrounding a slightly recessed area, meaning that the depth of the recessed area is less than the depth of the groove relative to the outer surface of the bearing member. As a further alternative, the recessed area is a completely recessed area, for example a cavity, circumferentially extending around at least a part of the outer surface of the bearing member, for example from one end of the nozzle inlet to the opposite end of the nozzle inlet (for example by 300°) so that the nozzle inlet is separated from the circumferential recessed area by non-recessed areas. The location, size including the angular extent of the recessed area is preferably designed so that it completely overlaps the corresponding outlet(s) of the cartridge.

The groove is preferably located at the surface of the bearing member between the nozzle inlet and the protruding cannula. In the plane of rotation, the angular offset of the groove and the nozzle inlet corresponds to the pivot angle between the first and second positions. The raised ridge preferably surrounds the cartridge outlet(s).

The groove on the outer surface of the bearing member is located so as to surround the outlet(s) of the cartridge when the nozzle is positioned in the first or storage position. In this first or storage position the groove is engaged with the corresponding raised ridge whereas when the nozzle is positioned in its second or operative position the raised ridge surrounds the inlet of the bearing member of the nozzle. The raised ridge thus seals with the outer surface of the bearing member. The engagement of the groove with the raised ridge in the storage position of the nozzle in turn forms a detent, which tends to improve the seal and to prevent accidental opening of the capsule.

Alternatively, the structure of the outer surface of the bearing member is a raised structure and the structure of the inner surface of the bearing shell is a corresponding recessed structure. For example, the outer surface of the bearing member comprises a raised ridge continuing along a closed curve or path, and the inner surface of the bearing shell comprises a corresponding groove. The raised ridge preferably surrounds the inlet of the nozzle, and the groove at the inner surface of the bearing shell is offset from the cartridge outlet(s). More preferably the groove is located so that the outlet(s) are beyond the area surrounded by the groove.

The raised ridge and the groove on the bearing member and the bearing shell respectively are preferably located so as to engage with one another when the nozzle is positioned in its first or storage position. Furthermore, the raised ridge surrounds the cartridge outlet(s) when the nozzle is positioned in the second position, whereas when the nozzle is positioned in the first position, the corresponding groove surrounds the inlet of the nozzle. The raised ridge thus seals with the inner surface of the bearing shell. The engagement of the groove with the raised ridge in the storage position of the nozzle in turn forms a detent, which tends to prevent accidental opening of the capsule.

According to another embodiment of the invention, the outer surface of the bearing member, for example of the nozzle, comprises a structured surface, but not necessarily the inner surface of the bearing shell. The structure of the outer surface of the bearing member is preferably a raised structure, such as a raised ridge, continuing along a closed curve or path. In this embodiment the bearing shell (of the cartridge, for example) comprises an aperture surrounding the raised structure of the bearing member at least in part, and extending from the inner surface of the bearing shell to the outer surface of the capsule. Preferably, in case the raised structure is not completely cleared by the aperture, the inner surface of the bearing shell comprises a recessed structure, such as a groove that at least in part corresponds to the raised structure of the outer surface of the bearing member.

Preferably the aperture surrounds at least the inlet of the nozzle when the nozzle is positioned in the first position, whereas when the nozzle is positioned in the second position the raised ridge surrounds the at least one cartridge outlet.

In the capsule of the invention, the cross-section of the groove preferably comprises a radius of approximately 0.25 mm and a depth of approximately 0.01 to 1.0 mm and preferably 0.05 mm. In another embodiment the groove comprises a radius of approximately 0.25 mm and a depth of approximately 0.075 mm and in still another embodiment the groove comprises a radius of approximately 0.5 mm and a depth of approximately 0.1 mm.

The bearing member is preferably elastically deformable, and, for example, made of a plastic material. Preferably the bearing member is tightly fit within the bearing shell to provide a tight seal between both parts when the nozzle is pivoted in either position. In the first or storage position the nozzle tightly closes off at least one outlet, whereas in the second or operative position a tight seal between both parts and in particular in the area surrounding the nozzle inlet/cartridge outlet(s) prevents leaking when the contained material is extruded from the cartridge through the nozzle.

The cartridge is preferably made of plastic material, such as polypropylene (PP), polyethylene (PE), acrylonitrile butadiene styrene (ABS), polyoxymethylene (POM). Preferably the cartridge is made of a polypropylene, such as Sabic 571 available from the Saudi Basic Industries Corporation Company of Riyadh, Saudi Arabia. Additionally, the plastic material may be glass or carbon fiber reinforced. Furthermore a grade of these plastic materials may be used having a higher tensile strength relative to the standard grades, such as Sabic 578.

The plastics material optionally comprises at least one friction-reducing additive (such as Kemamide® Ultra of Chemtura Corporation). The additive provides lubrication between the bearing member and the bearing shell. If an additive as described is included in the plastics material, the torque required to move the nozzle from its storage position to the operative position is reduced relative to the case where plastic is used without an additive.

The nozzle is preferably made of a plastic material, such as polycarbonate (PC), polystyrene (PS), polybutylene terephthalate (PBT), acrylonitrile butadiene styrene (ABS), polyoxymethylene (POM), polypropylene (PP), polyethylene (PE), and/or polyamide (PA). Preferably the nozzle is made of a polycarbonate, such as Makrolon® 2458, available from the Bayer AG Company of Leverkusen, Germany. Additionally, the plastic material may be glass or carbon fiber reinforced.

Preferably the nozzle and/or the cartridge are made of an opaque plastic material, and more preferably out of a material being opaque with respect to blue light, because blue-light curing dental materials may be stored in a capsule according to the invention, and they must not be exposed to blue light (including full-spectrum light) during storage.

A part of the capsule may comprise a color code, indicating the type and/or grade of the material contained in the capsule. Preferably the color of at least a part of the cartridge indicates the material type or class, and the color of at least a part of a plunger (which preferably is accommodated in the capsule to expel the material from the cartridge) indicates the material grade or shade.

The material of which the components of the capsule are made may comprise additives making them laser-engravable and/or laser-printable.

The nozzle optionally comprises a static mixer within the cannula, such as a static mixer having helical sections or a Quadro™ mixer of the type available from the Sulzer Chemtech Company of Switzerland. Preferably a static mixer has a largest dimension and/or diameter within a range of 0.7-2.3 mm, and in more particular within 0.7 and 2.1 mm. A preferred mixer has a diameter of 2.1 mm. A mixer having such dimensions allows the cannula to be made relatively compact, meaning with a rather small cross-sectional dimension and with a relatively short size. It has been found that a cannula appropriately designed for housing a mixer having dimensions within the specified ranges provides for good intra-oral use of the capsule, meaning good access to and visibility in small spaces.

The nozzle may also comprise a reinforcement element for reinforcing the section extending from the bearing member to the cannula. The reinforcement element is preferably a reinforcing web extending along the axis of the cannula. Such a web is preferred because the torque required to move the nozzle from its storage to its operative position may be relatively high. Alternatively, the cannula may comprise an ovular cross section with its long axis in the plane of rotation of the nozzle. The torque to move the nozzle from its storage to its operative position is preferably between 0.05 to 0.6 Nm and more preferably between 0.1 and 0.4 Nm.

The capsule of the invention preferably further comprises a locking mechanism to lock the nozzle in its operative position. The locking mechanism is formed by at least one detent provided at the bearing shell for engagement with the nozzle cannula. The capsule may further comprise a locking mechanism to releasably lock the nozzle in its storage position. The term "lock" or "locking" in this context generally includes releasably and permanently locking in position.

The capsule of the invention is filled, for example with a material of high viscosity, such as a dental filling material.

The capsule may also be filled with a material with low to medium viscosity, such as a dental impression material. Preferably, the capsule is filled with light-curable and/or chemically-curable material selected from among:
- a resin modified glass ionomer material,
- a resin modified luting material,
- a resin modified core build-up material,
- a resin based luting material,
- a resin based filling material,
- a resin based core build-up material,
- a temporary crown and bridge material, or any other material suitable to be used with the capsule of the invention. The materials are preferably paste materials and provided as one or more components.

The capsule of the invention is preferably manufactured by two-shot injection molding. In particular, the capsule is manufactured by first molding the nozzle with the bearing member, and subsequently molding the cartridge with the bearing shell around the bearing member. The capsule is preferably manufactured in its storage position so that the shape of the bearing shell mates with the shape of the bearing member in the storage position of the capsule.

The capsule of the invention preferably provides a certain sealing capacity when the nozzle is pivoted in its operative position, meaning that the sealing between the bearing member and the bearing shell can be maintained up to a certain pressure in the material, generated by the plunger when advanced to expel material from the chambers, until leakage occurs. The sealing capacity preferably corresponds to a pressure in the material of 40 to 160 bar, and preferably to 60 to 80 bar. In contrast, the sealing capacity in the storage position of the nozzle may be lower, because a high sealing capacity as required during dispensing material from the capsule is not necessary during the capsule storage which generally does not involve generation of high pressures.

Therefore it is possible to create an improved seal only shortly before use of the capsule which is of advantage, because it is not required to maintain a high pressure between parts of the surface of the bearing member and bearing shell over the storage time, which can be several months up to 3 and more years. Maintaining a pressure over such long time periods between plastic parts, as suggested for embodiments of the invention, would be difficult because of the relaxation properties plastic materials generally possess, and can thus be avoided.

According to a second aspect, the invention provides a combination of a capsule according to the first aspect with a handheld dispenser that can be used to push the material out of the capsule.

According to a third aspect, the invention provides a method of manufacturing the capsule of the invention, comprising the steps of molding the nozzle and subsequently molding the cartridge with the bearing shell around the bearing member. In this method, the nozzle comprises a structure forming the corresponding counter-structure at the bearing shell during molding of the capsule. The structure at the nozzle is preferably a groove or raised ridge, and the counter-structure a corresponding raised ridge or groove respectively. Preferably, the capsule is manufactured in its storage position. Alternatively, the bearing member of the nozzle comprises a specific cross-sectional shape (such as elliptical) which provides the bearing shell with a corresponding inner cross-sectional shape.

According to a fourth aspect, the invention provides the use of a nozzle comprising a bearing member for injection molding the capsule of the invention, preferably by a two-shot injection molding process.

It may be provided that the bearing member comprises at least one blind hole aligned with and corresponding to the outlet(s) of the cartridge when the nozzle is positioned in its storage or first position. This provides flash-free molding of the outlet(s). A "flash" in this context is undesirable excess material that during molding penetrates gaps between parts of the mold, or between the mold and the part to be molded around. Optionally or additionally the core(s) of the mold forming such outlets may comprise a sharp edge at its/their front for sealing with the nozzle during molding of the capsule.

It may be provided that the groove and/or the raised ridge of one of the bearing shell or bearing member comprises a profile selected from among a U-shape, a V-shape and a V-shape having rounded edges. The legs of such shapes may be symmetrical relative to a center axis of the profile, or have different angles relative to it. The edges formed by the transition of the profile and the surface of the bearing member/shell may be rounded.

It may be provided that the groove of the bearing member or/and the bearing shell comprises sections having different depths. Preferably such sections that are oriented transverse to the plane of rotation of the nozzle are different in depth, for example the section of the groove forming the front section on a movement of the nozzle being swiveled open is deeper than the other sections. Such a configuration reduces the forces required to move the nozzle and equalizes the forces occurring at the raised ridge which corresponds with the groove.

In turn it may be provided that the raised ridge of the bearing member or/and the bearing shell comprises sections having different heights. Preferably sections that are oriented transverse to the plane of rotation of the nozzle are different in height, for example the front section during a rotation of the nozzle being swiveled open is higher than the rear section. The other sections of the raised ridge form a continuous transition between the sections having different heights, so that the raised ridge overall preferably does not comprise sharp steps or differences in height. Such a configuration also reduces the forces required to move the nozzle and equalizes the forces occurring at the raised ridge. Preferred ranges for sections of different heights of the raised ridge are 0.02 mm to 0.06 mm for the section of a lower height and 0.15 mm to 0.3 mm for the section of a greater height. However, in a particular embodiment the section of a lower height is in a range of 0.02 mm to 0.4 mm and the section of a greater height is in a range 0.15 mm to 0.5 mm. Preferably the first section has a height of 0.02 mm, more preferably 0.15 mm, and the latter a height of 0.3 mm. The following table shows further examples of preferred combinations:

| lower height of raised ridge in mm | greater height of raised ridge in mm |
|---|---|
| 0.02 | 0.30 |
| 0.04 | 0.08 |
| 0.06 | 0.12 |
| 0.06 | 0.15 |
| 0.15 | 0.24 |
| 0.25 | 0.30 |

It may be provided that both the bearing member and the bearing shell have a groove and a raised ridge. In this case the raised ridge of the bearing member and the raised ridge of the bearing shell are adapted to face one another (e.g. seal with one another) when the nozzle is positioned in its second position.

It may be provided that both the bearing member and the bearing shell comprise a structure selected from among a groove, a raised ridge, a recessed area and a raised area, wherein one of the structures faces another one of the structures in either position of the nozzle.

In one embodiment of the invention the bearing member comprises a bearing section and a pin, wherein the pin is arranged in an off-center relationship at a side face of the bearing section. The bearing section is preferably sized and shaped such that it matches the size and shape of the bearing shell in the first and second position and in at least one position between. Preferably the bearing section is of a generally cylindrical shape. Further, the pin may be of a generally cylindrical shape. The bearing member may also comprise two pins with the bearing section arranged therebetween. Because of the off-center arrangement of the pin(s) and the bearing section the shape of the bearing member and the shape of the bearing shell generally match in the first position of the nozzle, but generally differ from each other in the second position of the nozzle.

Another embodiment of the invention is related to a nozzle having a nozzle inlet and a raised lip. The raised lip of this embodiment comprises a leading section and a trailing section, wherein when the nozzle is positioned in the first position at least a part of the leading section projects from an outer surface of the bearing shell and at least a part of the trailing section projects from an inner surface of the nozzle inlet. In contrast, when the nozzle is positioned in the second position the leading section and the trailing section may at least partially project into the nozzle inlet. Further, when the nozzle is positioned in the second position the leading section and the trailing section may form a continuous structure that projects into the nozzle inlet. Preferably, when the nozzle is positioned in the second position the leading section and the trailing section form a flexible lip seal for sealing with an inner surface of the bearing shell.

Still another embodiment is related to a method of forming a raised lip that has a leading section and a trailing section, wherein at least a part of the leading section projects from an outer surface of the bearing shell and at least a part of the trailing section projects into a nozzle inlet, the method comprising the steps of:
  i. molding a raised lip that protrudes from an outer surface of the bearing member; and
  ii. deforming a part of the raised lip such that it is adapted to project into the nozzle inlet.

In one embodiment the cartridge is composed of at least a cartridge front portion of a first plastic material and a cartridge rear portion of a second plastic material. The cartridge front portion and the cartridge rear portion are connected by material bond provided by the first and second plastic materials. The cartridge front portion of this embodiment at least provides the bearing shell. The cartridge front portion may comprise outlet channels for the dental material which are inclined with respect to one another and merge at the bearing shell.

Another embodiment is related to a method of molding a cartridge. The cartridge bears a pivotable nozzle and comprises the steps of:
  i. providing the nozzle in a mold for molding a cartridge front portion;
  ii. molding a cartridge rear portion; and
  iii. molding the cartridge front portion around at least a part of the nozzle;
wherein one of the cartridge front portion and cartridge rear portion is substantially solid when the respective other part is molded. The cartridge rear portion may be provided in a mold for molding the cartridge front portion, and cartridge front portion bearing the nozzle may be provided in a mold for molding the cartridge rear portion.

In yet another embodiment the capsule comprises a window between two chambers of the cartridge for holding components of a dental material and the bearing shell of the cartridge. The window may form a hole through the capsule.

In a further embodiment of the invention the cartridge of the capsule comprises at least one chamber for holding a component of a dental material. The chamber preferably has a front wall and an opposite wall forming at least a part of the bearing shell of the cartridge, wherein the chamber front wall is spaced from the wall forming the bearing shell or a part of it.

In another embodiment of the invention the nozzle comprises a mixing channel that provides a first inlet into the mixing channel, and further, a second inlet merging with the mixing channel.

In one embodiment of the invention the capsule comprises at least one material chamber for holding a dental material, and an annular ridge on the outer surface of the bearing member of the nozzle. The annular ridge preferably provides a part of the material chamber(s) when the nozzle is in the first position. Further the annular ridge may comprise a groove which provides a fluid pathway with the material chamber(s) when the nozzle is in the second position. The groove is preferably in permanent fluid communication with a mixing channel of the nozzle.

In another embodiment of the invention the capsule comprises an indicator for indicating an amount of material remaining in the capsule. The indicator may indicate the last 30% of material remaining in the capsule, for example. The indicator may also continuously indicate the remaining material in the capsule from a state in which the capsule is full to a state in which the capsule is empty. The indicator may comprise a window in the cartridge, and further an indicator member which is connected to a piston within the capsule. The indicator further may comprise a scale which in co-operation with the indicator member provides for indicating a proportional amount of remaining material. For example the scale may by a triangle with the vertex representing a low amount of remaining paste and the leg opposite of the vertex representing a high amount of remaining paste. The indicator further may comprise a scale which in co-operation with the indicator member provides for indicating an absolute amount of remaining material. For example, the scale may comprise indicia showing absolute values of an amount of material remaining in the capsule. Preferably such indicia are laser engraved in the cartridge.

In another embodiment of the invention the capsule comprises at the nozzle a retention member for retaining an extension tip on the nozzle. Such extension tip may, for example be useful to elongate the nozzle or to reduce the outer diameter of the nozzle.

In a further embodiment of the invention the capsule comprises a rim at the rear-most end of the cartridge and a groove in a distance in front of the rim. The groove is preferably adapted to engage with a ridge of an applicator for use with the capsule. The rim may provide a security feature in that it may prevent the capsule from separating from the applicator in case the ridge moves out of the groove. This may, for example, happen in case the capsule is overloaded by applying too much force to it through the applicator.

The described structures of the present invention may also be used for one or multi-component syringes, e.g. for use in dentistry.

The present invention provides good seating between the nozzle and the cartridge during dispensing of a substance, even for high extrusion pressures and for standard tolerances of molded parts. Thus, the capsule of the invention can be used for a broader variety of substances, especially for highly-viscous substances, but also with dimensions of the passageway of the nozzle which may be rather small (for example 2 mm) and therefore otherwise form a bottleneck for the material flow.

The present invention further provides easy assembly using only a few parts, which saves material and labor costs. Furthermore the present invention reduces the effort necessary to mold parts of a precise size. In contrast to using two parts being assembled with each other and both having molding tolerances, molding of a second part around a first compensates for the tolerances of the first part. In other words one shape determines the shape of the other, and only tolerances of the second part have an effect. Therefore a good seal for storage of the material stored in the capsule is created automatically, during manufacturing, and not as a result of the manufacturing tolerances of two individual parts.

BRIEF DESCRIPTION OF THE DRAWINGS

Preferred embodiments of the invention are described in more detail below with reference to the attached drawings, which are by way of example only.

FIG. 8a is a perspective view of the capsule of the third embodiment of the invention, wherein the capsule is shown in its storage position;

FIG. 8b is a partial cross-sectional view of FIG. 8a on a larger scale;

FIG. 9a is a perspective view of the capsule of the third embodiment of the invention, wherein the capsule is shown in its operative position;

FIG. 9b is a partial cross-sectional view of FIG. 9a on a larger scale;

DETAILED DESCRIPTION OF PREFERRED EMBODIMENTS

Figure 2:
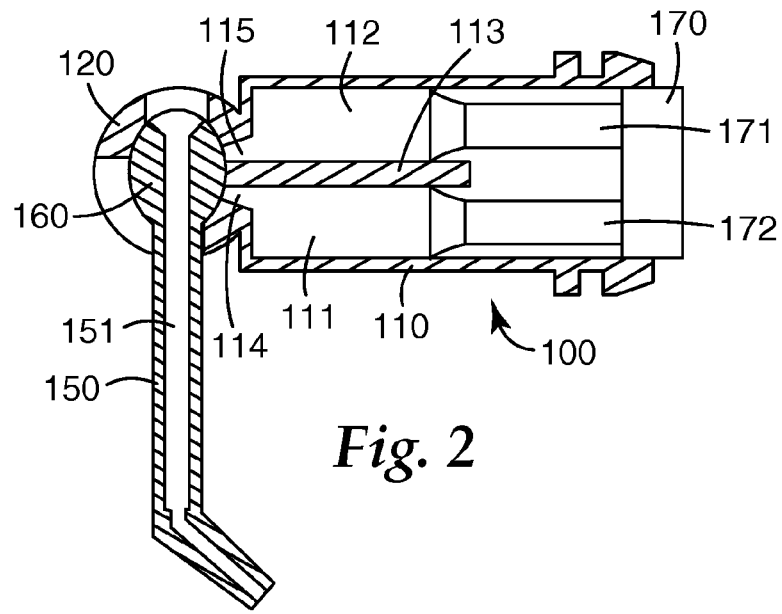
FIG. 2 is a schematic cross-sectional view of a capsule according to a first embodiment of the invention, wherein the capsule is shown in its storage position.
Figure 3:
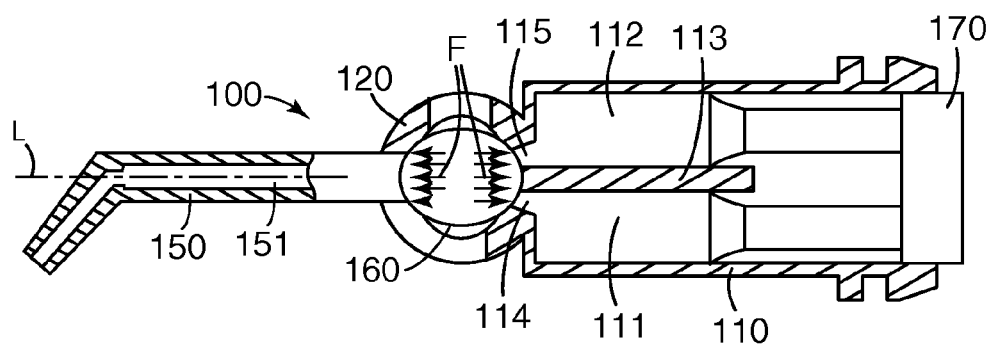
FIG. 3 is a schematic cross-sectional view of a capsule of FIG. 2, wherein the capsule is shown in its operative position.

FIG. 2 is a schematic cross-sectional view of a capsule 100 according to a first embodiment of the invention. In FIG. 2, the capsule 100 is shown when it is closed for storage, that is when the nozzle 150 is positioned in its first or storage position; FIG. 3 shows the capsule 100 of this embodiment when the nozzle 150 is positioned in its second or operative position. Typically, the two positions differ by approximately 90° of rotation of the nozzle.

Figure 1:
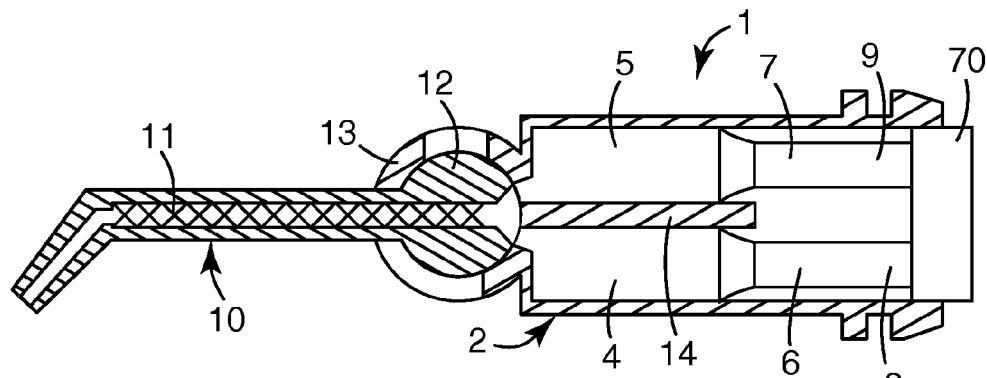
FIG. 1 is a schematic cross-sectional view of a known capsule.

Capsule 100 comprises a cartridge 110 having a first chamber 111 for containing a first material component, and a second chamber 112 for containing a second material component. The two chambers 111, 112 open into outlets 114, 115. A plunger 170 comprising two pistons 171, 172 is accommodated in the cartridge and adapted to expel the components from the chambers 111, 112. A common partition wall 113 separates the two chambers 111, 112 from one another. A nozzle 150, in which a static mixer 11 may be arranged (shown in FIG. 1), is pivotably and/or displaceably accommodated in a bearing shell 120. The nozzle 150 comprises a bearing member 160 which is preferably joined with bearing shell 120 of cartridge 110, for example by a press-fit, and closes off the outlet(s) of the cartridge 110. When the nozzle 150 is positioned in a first position (as shown in FIG. 2), the outlets 114, 115 of the cartridge 110 are closed off by the bearing member 160 of the nozzle 150 and, when the nozzle 150 is positioned in a second position (as shown in FIG. 3), the outlets 114, 115 are connected to the passageway 151 of the nozzle 150.

In the embodiment of FIGS. 2 and 3, the bearing member 160 of nozzle 150 has a non-circular cross-sectional shape, specifically an elliptical shape, in the plane of rotation of the bearing member 160 relative to the cartridge 110. In the storage position (FIG. 2) of the nozzle 150, the size and shape of the bearing member 160 matches the size and shape of the bearing shell 120. However, in the operative position (FIG. 3) of the nozzle 150, the size and shape of the bearing member 160 mismatches or differs from the size and shape of the bearing shell 120. This is possible because the bearing shell 120 of the cartridge 110 is elastically deformable. In the storage position, the bearing member 160 of the nozzle 150 closes the outlets 114, 115 of the component chambers 111, 112. Upon swiveling the nozzle from the storage position into the operative position, the inlet of the nozzle 150 is brought in fluid communication with the outlets 114, 115 of the component chambers 111, 112 so that material can be dispensed from the component chambers 111, 112 through the nozzle passageway 151. The extent of the mismatch in size and/or shape should be sufficient to create an improved seal, for example due to an increased compressive force, between the bearing member and the bearing shell so that the one is pressed against the other.

Figure 4:
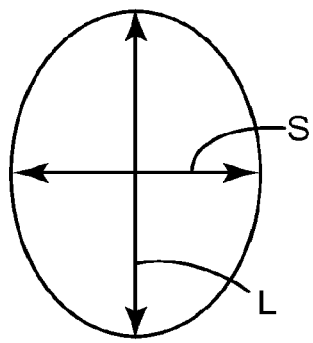
FIG. 4 is a schematic view of the bearing member of the capsule of FIG. 2.

In the storage position of the capsule, the short axis S (see FIG. 4) of the elliptical bearing member 160 is aligned substantially parallel to or coincident with the longitudinal axis of the capsule 100. In the operative position, the long axis L of the elliptical bearing member is aligned substantially parallel to or coincident with the longitudinal axis of the capsule 100 (see FIGS. 3 and 4).

The capsule is preferably manufactured by first molding the nozzle 150 (including the bearing member), and then molding the cartridge 110 around the bearing member 160. Because the bearing is elliptical, the bearing shell 120 will be elliptical as well. Because both parts have an elliptical cross-section, the bearing member 160 will be retained within the bearing shell 120, when the nozzle is in its operative position. In other words, the bearing member 160 will be put under a compressive force F along its long axis L (see FIG. 3) in the operative position of the nozzle. This compressive force results from the elastic deformation of the bearing shell 120, and provides improved sealing between the nozzle 150 and the cartridge 110 during application of material from the capsule. The difference in size of the bearing member between the short axis S and the long axis L (FIG. 4), and the deformability or flexibility of the bearing shell, is such that a manual rotation of the nozzle 150 is still possible.

Figure 5:
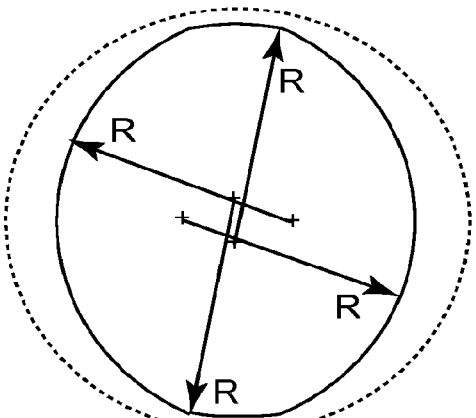
FIG. 5 is a schematic view of an alternative bearing member of the capsule of the invention.

As an alternative to having an elliptical bearing member 160, the cross-section of the bearing member may be composed of several curved segments, as shown in FIG. 5, but is not circular. With this configuration, the curvature at the extended dimension of the bearing member cross-section corresponds to the radius of the reduced dimension of the bearing shell cross-section. The cross-section is designed in a manner that when the nozzle is turned into the operative position, the curvature (at the extended dimension) of the bearing member of the nozzle will still conform to the curvature of the bearing shell in the area around the inlet of the nozzle. This provides optimum sealing between both parts in the first as well as in the second position of the nozzle. Noncircular deviations of the curvature at the nozzle may also be provided, to compensate for inaccuracies resulting from the elastic deformation of the bearing shell.

Figure 6:
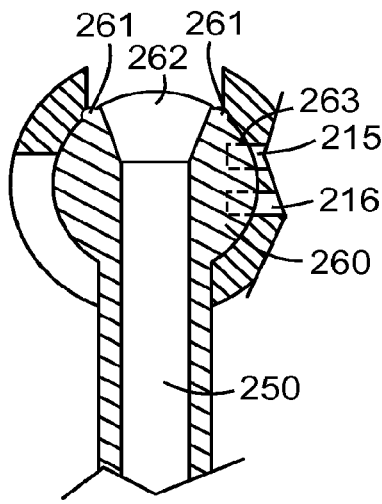
FIG. 6 is a schematic cross-sectional view of a capsule according to a second embodiment of the invention, wherein the nozzle is shown in its storage position.

FIG. 6 shows a second embodiment of the invention. In this embodiment, the bearing member 260 is of circular cross-section, and comprises a raised ridge 261 around the inlet 262 of the nozzle 250. In one embodiment, the bearing member may comprise at least one blind hole 263 aligned with and corresponding to the outlet(s) of the cartridge when the nozzle is positioned in its storage or second position. FIG. 6 shows the nozzle 250 in its storage position. Once the nozzle has been swiveled to the operating position, the raised ridge 261 is located such that it surrounds the outlets 215, 216 of the component chambers, and provides improved sealing in this area.

Figure 7:
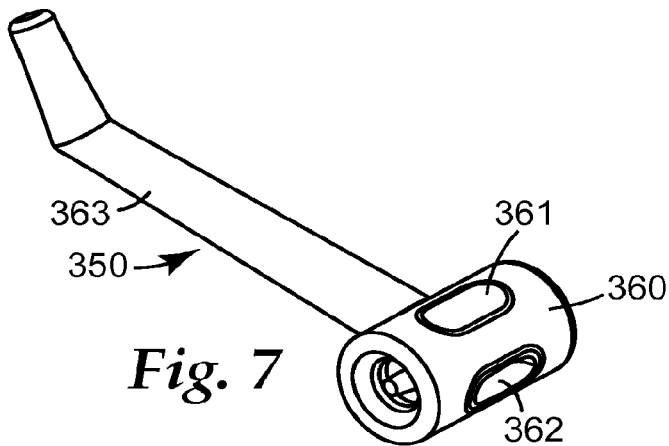
FIG. 7 is a perspective view of the nozzle of a capsule according to a third embodiment of the invention.

A third embodiment of the invention is shown in FIGS. 7 to 9. In this embodiment, nozzle 350 comprises bearing member 360 further comprising a substantially cylindrical outer surface. At this surface an inlet 362 is located generally opposite to the protruding cannula 363. Further at the outer surface of the bearing member 360 a groove 361 is located between the inlet and the cannula. In other words, with regard to a center axis of the cylindrical outer surface, the angular orientation of the inlet 362, the groove 361 and the cannula 363 are preferably 0°, 90° and 180° respectively.

In FIGS. 8a and 8b, nozzle 350 is shown co-injection molded with cartridge 310 in a partial cross-sectional view. In the storage position of the nozzle 350 shown in FIGS. 8a, 8b, the groove 361 of the bearing member 360 surrounds the two outlets 314, 315 of the component chambers of the cartridge 310. In this embodiment the cartridge 310 is molded via a two-shot injection molding process around the nozzle 350 in the storage position, and therefore a raised ridge 330 is formed at the bearing member 360 of the cartridge due to recessed replication of the groove 361. Like the groove, the corresponding raised ridge surrounds the outlets 314, 315.

As soon as the nozzle is moved to the operative position, the raised ridge 330 formed in the groove 361 leaves the groove 361, i.e. is angularly displaced from the groove 361, and the nozzle inlet 362 is rotated towards the raised ridge 330. Thus, in the operative position (shown in FIGS. 9a, 9b), the raised ridge 330 at the bearing shell 320 of the cartridge 310 provides a tight seal against the surface of the bearing member 360 of the nozzle 350, especially around the nozzle inlet 362.

Figure 10:
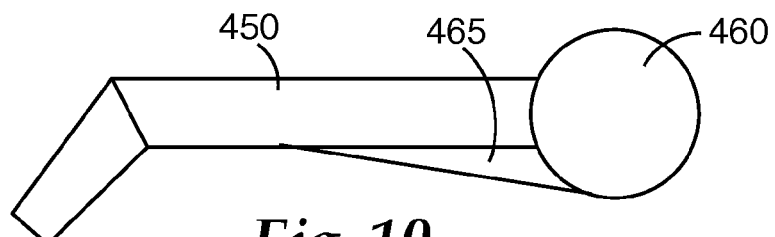
FIG. 10 is a schematic view of a preferred nozzle design, having a reinforcement web.

FIG. 10 shows a nozzle 450 that comprises a reinforcing web 465. Because the cannula is used to move the nozzle 450 from its storage position to its operative position, which requires a certain level of force to be applied to the cannula, web 465 is incorporated to provide increased rigidity and stability to the cannula. Alternatively, the nozzle is reinforced by designing the cannula with an oval shaped cross-section with the longer axis of the oval being in the same plane as the direction of the force applied to rotate the nozzle.

Figure 11A:
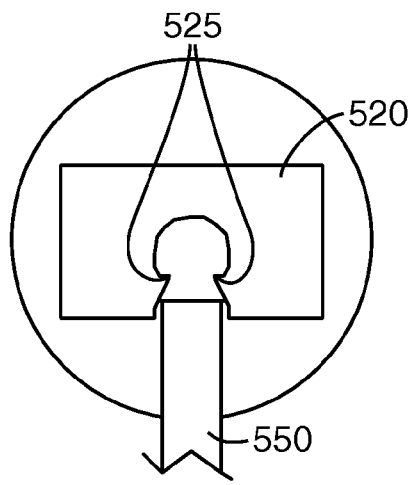
FIGS. 11a, 11b are schematic views showing the locking mechanism locking the nozzle to the cartridge in the operative position of the capsule.
Figure 11B:
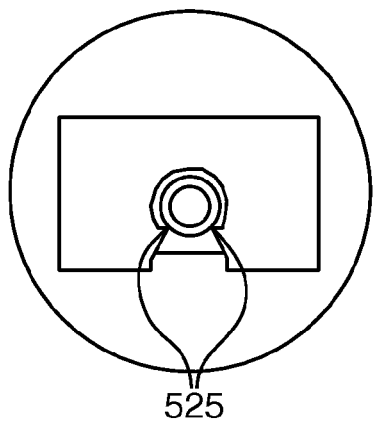
Figure 11C:
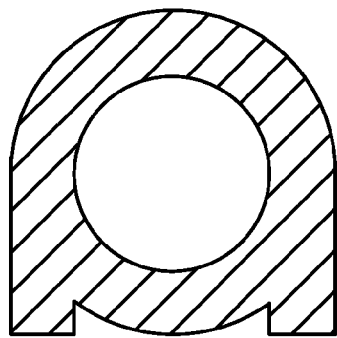
FIGS. 11c, 11d are schematic views showing alternative cross-sections of the nozzle of alternative locking mechanisms.
Figure 11D:
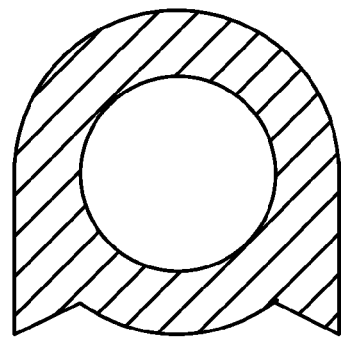

The capsule of the invention preferably comprises a locking mechanism. This is shown in FIGS. 11a through 11d. The locking mechanism is formed in this example by two detents 525 formed at the bearing shell 520, which engage with the nozzle 550 as soon as it has been moved completely into the operative position (FIG. 11b). This provides feedback to the user (tactile and/or audible) about the correct positioning of the nozzle relative to the cartridge, especially if the friction between the bearing member and the bearing shell is high. Optionally the nozzle may comprise a structure for engagement with the detents 525, for example the nozzle may comprise a D-shaped cross-section. The D-shape may comprise cross-sections as shown in FIGS. 11*c* and 11*d* or a classic D-shape. Shapes as shown in FIGS. 11*c* and 11*d* provide for better molding quality because the wall thicknesses are more uniform relative to the classic D-shape, which would cause depressions at areas close to or at thick walls. It may also be provided that the locking mechanism is irreversible, meaning that once the cannula has been moved to its operative position a reverse movement is prevented. Alternatively or in addition, the nozzle is releasably locked in its storage position to avoid unintentional opening of the nozzle which would have an impact on storage stability.

Figure 12:
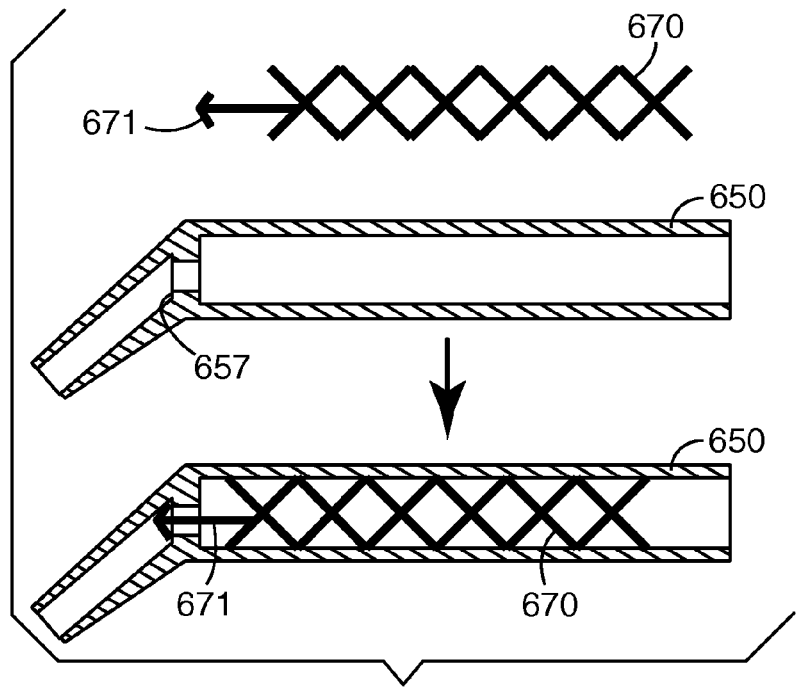
FIG. 12 is a schematic view of a static mixer according to the invention, being shown outside of and within the nozzle of the capsule.

A preferred static mixer 670 is shown in FIG. 12. The static mixer 670 comprises a retention member 671 that prevents the mixer 670 from falling out of the nozzle during transport. The retention member 671 is engageable with a corresponding flange 657 within the nozzle 650 and adjacent to the dispensing tip. Alternatively, the mixer consists of one or more mixing elements that have a diameter slightly larger than the interior of the nozzle. Furthermore, the nozzle may preferably have zones of a reduced diameter providing for clamping the mixer in the nozzle. An advantage of having a nozzle with reduced areas is that the static mixer can be molded at a uniform diameter over its length, thus, because the mixer is symmetric, it can be inserted into the cannula at any orientation, i.e. with its front or its rear end forward. The enlarged or reduced diameter may extend cylindrically or conically over its length. According to a further alternative, the mixer is initially molded in a curved shape so as to achieve retention by friction as soon as the mixer is assembled in the nozzle. In case the nozzle is curved the mixer may be molded straight to facilitate the retention. It may be provided that the passageway of the cannula comprises a rectangular cross-section, or one of any other desired shape.

Figure 13A:
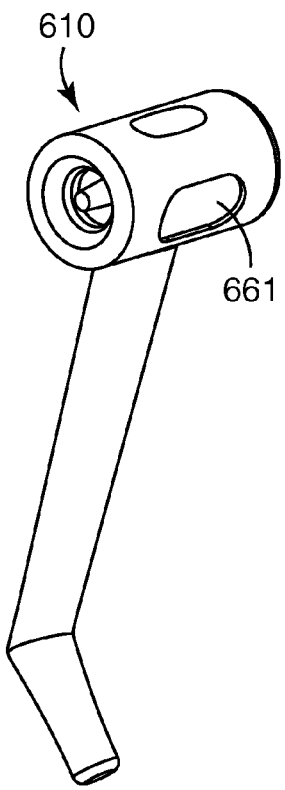
FIGS. 13a, 13b are perspective views showing the nozzle with different recessed areas according to alternative embodiments of the invention.
Figure 13B:
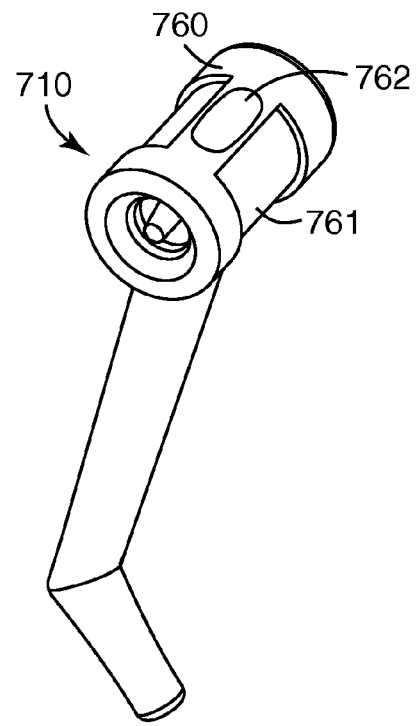

FIGS. 13*a* and 13*b* show embodiments of the present invention having recessed structures in the form of a completely recessed area 661, 761, in contrast to a groove surrounding a non-recessed area. In FIG. 13*a* the nozzle 610 comprises a recessed area 661 having a size to extend over the outlet(s) of the cartridge (not shown) when the nozzle 610 is positioned in its first or storage position. The recessed area 661 preferably completely overlaps the outlet(s) outside of their boundaries. It may also be provided that the nozzle of this embodiment has multiple such recessed areas for each corresponding outlet of the cartridge.

As shown in FIG. 13*b* the recessed structure may further be a recessed area 761 which circumferentially extends around at least a part of the outer surface of the bearing member 760, for example from one end of the nozzle inlet to the opposite end of the nozzle inlet (for example by 300°) so that the nozzle inlet 762 is separated from the circumferential recessed area 761 by non-recessed areas. The location and size including the angular extension of the recessed area 761 is designed to extend over the outlet(s) of the cartridge, meaning that the recessed area 761 completely overlaps the outlet (s) outside their boundaries.

Figure 14A:
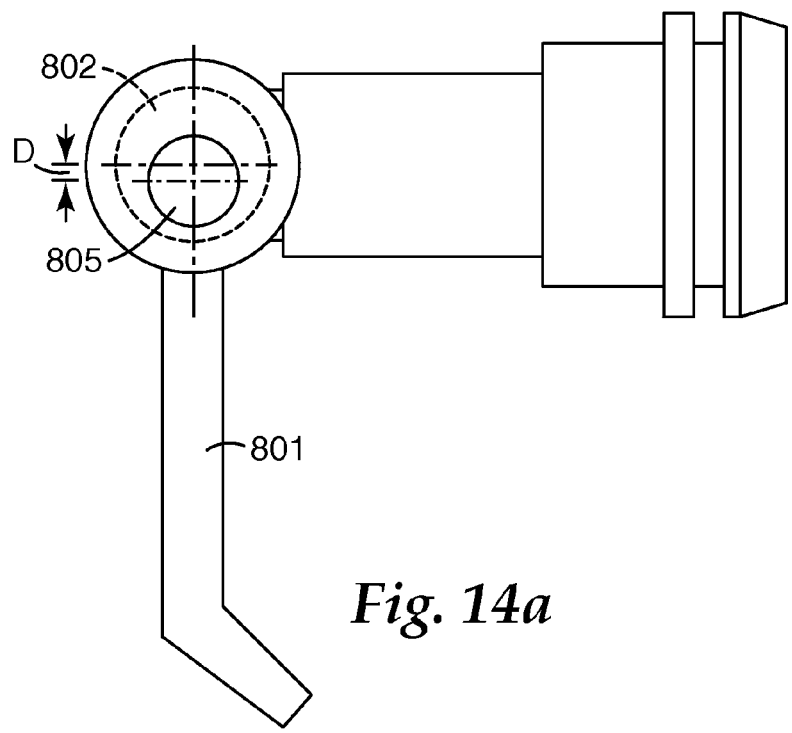
FIGS. 14a, 14b are schematic views of a cartridge having a nozzle with a bearing section and pins according to an embodiment of the invention.
Figure 14B:
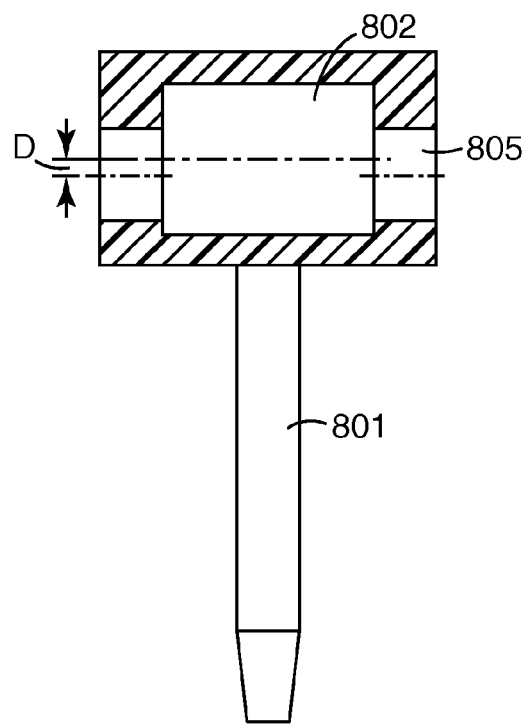

FIGS. 14*a* and 14*b* show an embodiment of a nozzle 801 having a bearing member comprising a generally cylindrical bearing section 802 and substantially cylindrical pin 805 protruding from the side faces of the bearing section 802. The pins 805 are arranged with their center axes offset (indicated by distance D in FIG. 14*b*) from the center axis of the bearing section 802. As an advantage the bearing section 802 generally matches in shape with the shape of the bearing shell 803 in the storage position, the operating position, and in any position therebetween. For this reason also the bearing section 802 and the bearing shell 803 may seal well with one another independent of the pivot position of the nozzle. On the other hand, the off-center arrangement of the pins improves the seal between the bearing member and the bearing shell when the nozzle is pivoted from the first to the second position. This is achieved in this embodiment because the pins are, as shown, offset in a direction substantially toward the end of the nozzle (in FIGS. 14*a*, 14*b* toward the top of the page). Therefore, if the nozzle is moved from the storage position to the operating position (a rotation of approximately 90 degrees in the illustrated embodiment), the bearing section is pushed back by the pins in a direction generally toward the capsule so that the pressure between the bearing member and the bearing shell at surfaces adjacent the outlets of the cartridge (not shown) is increased. This also preferably results in an improved seal, for example during dispensation of material from the capsule.

Figure 15A:
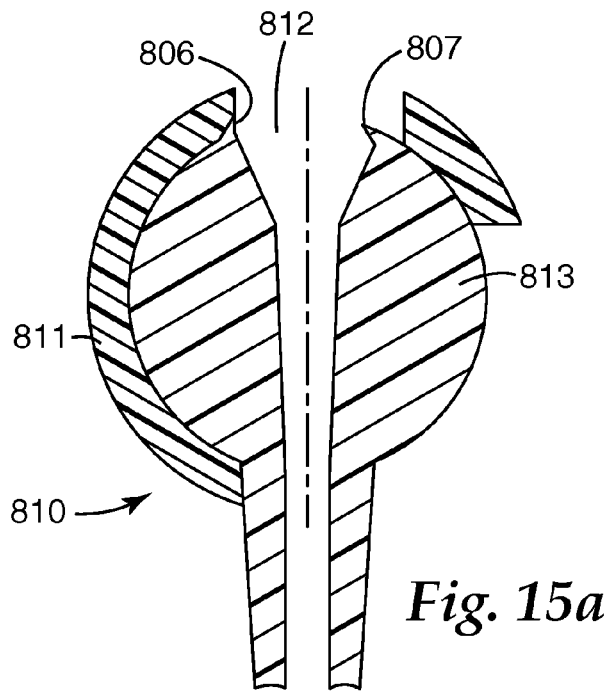
FIGS. 15a, 15b are cross-sectional views of a capsule having a raised lip according to an embodiment of the invention.
Figure 15B:
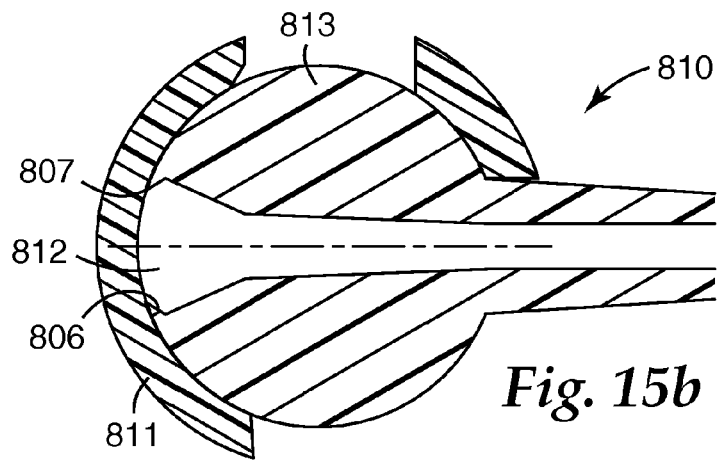
Figure 16:
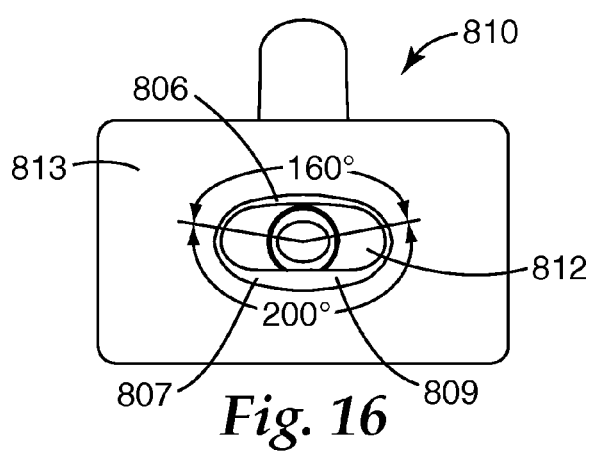
FIG. 16 is a view on the bearing member of the nozzle according to an embodiment of the invention.
Figure 17:
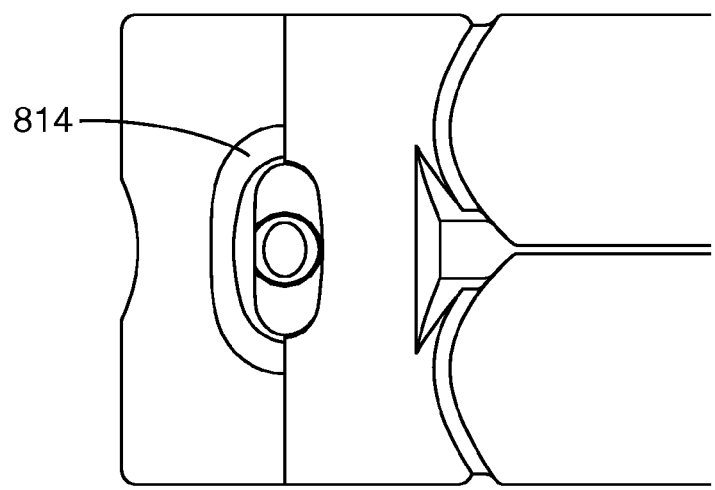
FIG. 17 is a perspective view on a capsule front area showing a raised lip according to an embodiment of the invention.

FIG. 15*a* and 15*b* show a nozzle 810 having a raised lip 809 (indicated in FIG. 16) on the bearing member 813 at the opening of the nozzle inlet 812. The raised lip 809 has a leading section 806 and a trailing section 807. In the example shown in FIG. 16, the leading section 806 surrounds approximately 160 degrees of the inlet opening, and the trailing section 807 extends inside the inlet opening along the remaining approximately 200 degrees of the inlet opening. As can be seen, the leading section 806 of the raised lip 809 in the initial storage position of the nozzle (shown in FIG. 15*a*) generally protrudes away from the outer surface of the bearing member 813 (in the figure upwards), and thereby leaving the inlet 812 open. In contrast, the trailing section 807 at least partially projects from a surface of the inlet 812 (extends laterally in the figure), and therefore extends laterally into the inlet 812. When the nozzle 810 is moved from the storage position toward the operating position (shown in FIG. 15*b*) the leading section 806 of the raised lip 809 deflects backward as soon as it is forced under the bearing shell so that it also extends laterally into the inlet. The trailing section 807, however, because it is already accommodated within the inlet generally retains its shape. Therefore the leading and trailing sections 806, 807 together form a generally circumferential lip 814 (shown in FIG. 17) inside of the inlet. As an advantage, once the nozzle is moved into the operating position the circumferential lip 814 provides an improved seal between the bearing member and the bearing shell 811. A further advantage may be provided when material is dispensed because the circumferential lip 814 may be pressed onto the inner surface of the bearing shell (around the outlet(s) of the cartridge) in response to the pressure built up during dispensation of the material. The configuration of the trailing section being accommodated in the inlet may provide the advantage that the trailing section is better protected from deflection away from the inlet during movement of the nozzle toward the operating position. Deflection may damage an unprotected trailing section, or impair the sealing effect.

The different configurations of the leading and trailing sections 806, 807 of the lip 809 further may provide the advantage that the nozzle 810 can be easily molded. Because a circumferential lip forms an undercut with respect to a mold core that is removed from the inlet, the removal of the nozzle from the mold may result in damage to the lip. The configuration of the leading edge, in which it does not protrude into the inlet, facilitates removal from the mold and helps to avoid damage to the lip, because the trailing section may be deflected more easily than an entire circumferential lip.

Figure 18:
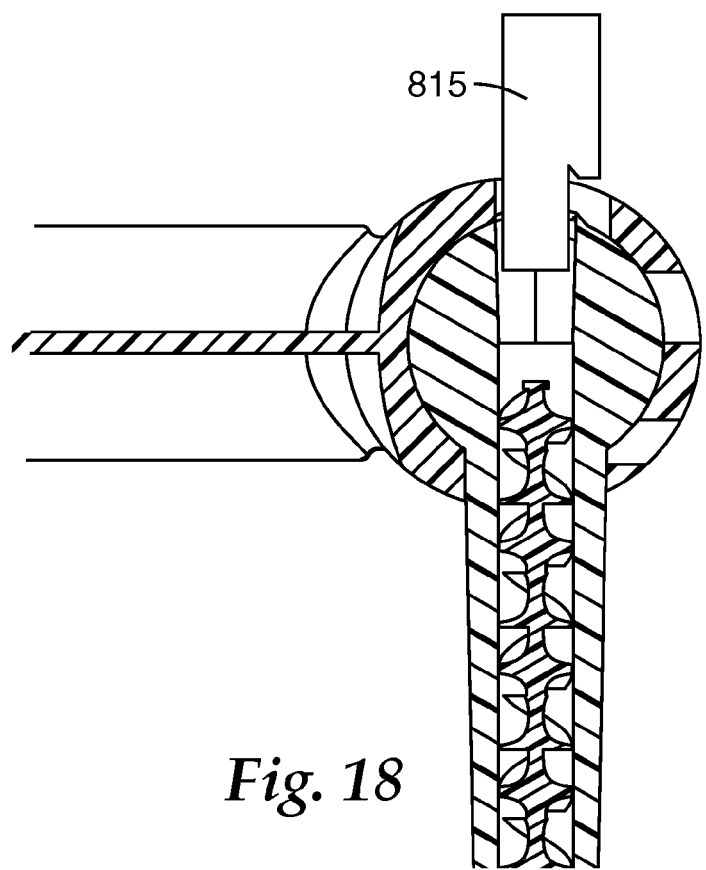
FIG. 18 is a cross-sectional view of a capsule having a nozzle with a raised lip and also showing a deformation tool according to an embodiment of the invention.

The raised lip 809 may also be molded as a structure entirely surrounding the inlet opening and protruding away from the outer surface of the bearing member. This structure may subsequently deformed, for example by a forming tool 815 as shown in FIG. 18, for example by hot or cold forming, to form a raised lip 809 having two differently configured sections 806, 807 as described.

Figure 19A:
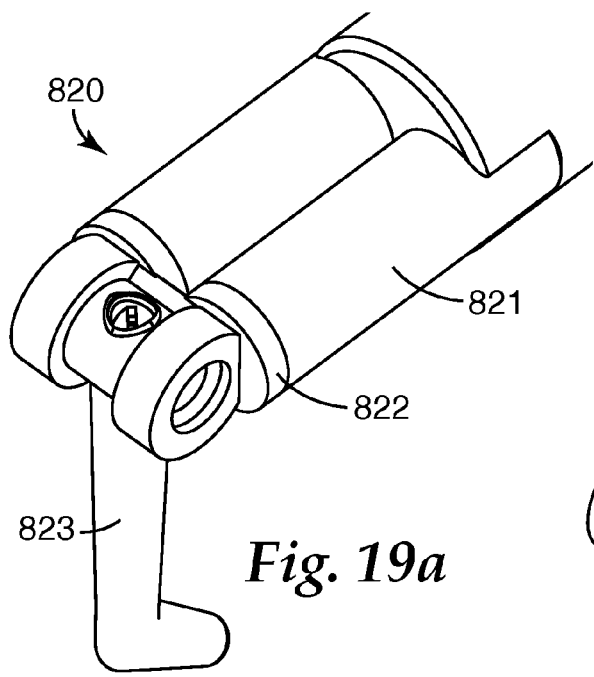
FIGS. 19a, 19b are perspective views of a capsule having a cartridge front portion and a cartridge rear portion according to an embodiment of the invention.

In FIG. 19a a capsule 820 is shown having a cartridge that comprises a cartridge front portion 822 and a cartridge rear portion 821. The cartridge front portion comprises a bearing shell for cooperation with a bearing member of a nozzle 823. The bearing member and the bearing shell of this embodiment may be configured according to any embodiment according to the invention as described herein. The cartridge front portion 822 is preferably two-shot molded with the nozzle 823 (see FIG. 19b). T his means that preferably the nozzle 823 is pre-molded and inserted in a mold for molding the cartridge front portion 822, and the cartridge front portion 822 is preferably molded around a part of the nozzle 823 to form a movable connection. The cartridge front portion 822 may also be two-shot molded with the nozzle 823 and the cartridge rear portion 821, meaning that a pre-molded nozzle 823 and a pre-molded cartridge rear portion 821 may be disposed in a mold and the cartridge front portion 822 may be molded to connect both parts. In that case the cartridge front portion 822 preferably bonds to the cartridge rear portion 821 (for example by using the same material, such as polypropylene, for both parts), but not to the nozzle 823.

The cartridge front portion 822 of this embodiment preferably tightly encloses the bearing member of the nozzle so as to provide a good seal between the bearing member of the nozzle 823 and the bearing shell of the cartridge front portion 822. The nozzle 823 in this case is still movable, for example because the nozzle may be made of a plastic material that is different from the plastic material used for the front portion. A suitable combination is, for example, polycarbonate and polypropylene, wherein preferably the pre-molded part is made of the plastic material having the higher temperature stability (in this case polycarbonate). An advantage of this embodiment may be provided by the possibility of molding a relatively small part (the cartridge front portion 822) around the nozzle 823. Therefore the cooling of the cartridge front portion 822 can be optimized to achieve low distortion and to help to avoid inhomogeneous shrinkage. This further helps to optimize the accuracy of the shape of the cartridge front portion 822 and the nozzle which is important to achieve a good seal between both parts. As another advantage the heat impact on the nozzle 823 during molding of only the cartridge front portion 822 is reduced relative to two-shot molding of the complete cartridge with the nozzle. Thereby the force required to move the nozzle may be optimized, for example controlled within certain ranges.

Figure 20:
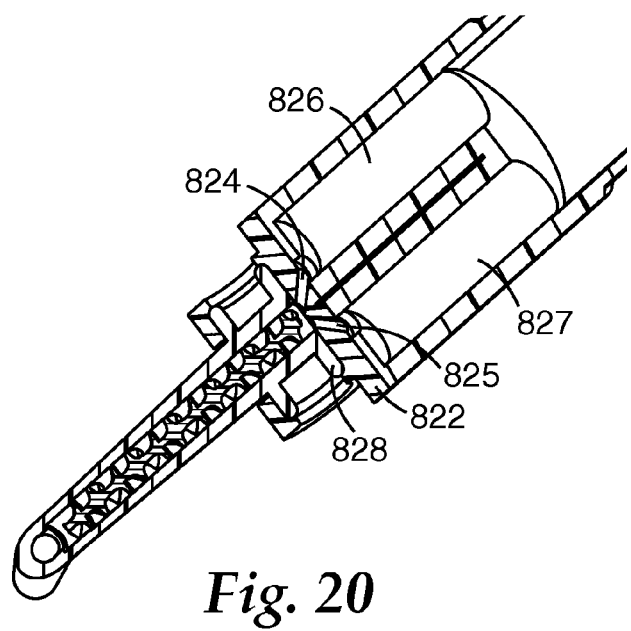
FIG. 20 is a cross-sectional view outlining outlet channels within a capsule according to an embodiment of the invention.

Another advantage may arise from molding the outlets 824, 825 of the cartridge in a configuration as shown in FIG. 20. This embodiment allows the mold cores that may be used to form the outlets to be arranged and moved at an angle relative to each other. Therefore the outlets 824, 825 may be arranged at an angle relative to each other. The angle may be selected so that the outlets 824, 825 merge adjacent the inner surface of the bearing shell 828. This provides the possibility of minimizing the area of the outlet openings, and therefore also the possibility of minimizing the inlet area of the nozzle. In consequence, the force eventually built up between the nozzle and the cartridge due to pressure generated during dispensation of material may be reduced, so that the quality of the seal required between the cartridge and the nozzle may be less.

It is another advantage of this embodiment that the wall thicknesses of the cartridge front portion 822 may be optimized because the front portion 822 may be designed accordingly without being limited by requirements necessary for the end portion 823. In other words, the split design of the front portion 822 and the end portion 823 may also reduce the technical limitations presented by an integral design.

Figure 21:
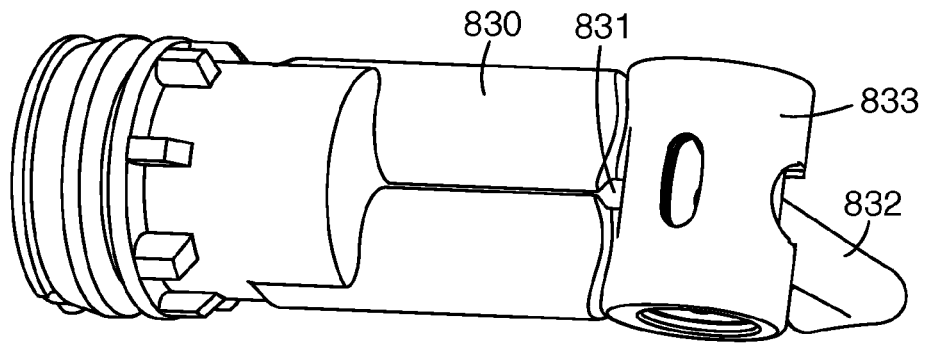
FIG. 21 is a perspective view of a capsule having a window according to an embodiment of the invention.

In FIG. 21 an embodiment is shown comprising a recess or window 831 in the cartridge 830. The cartridge has a cartridge front 833 that receives the nozzle 832. The cartridge front 833 and the nozzle 832 in co-operation preferably form a movable connection with a tight seal therebetween. The window 831 as outlined may help to reduce the plastic material accumulation at the cartridge front 833, and therefore may provide for improved shape accuracy of the cartridge front 833. Therefore an improved seal of the cartridge front 833 with the nozzle 832 may be achieved.

Figure 22:
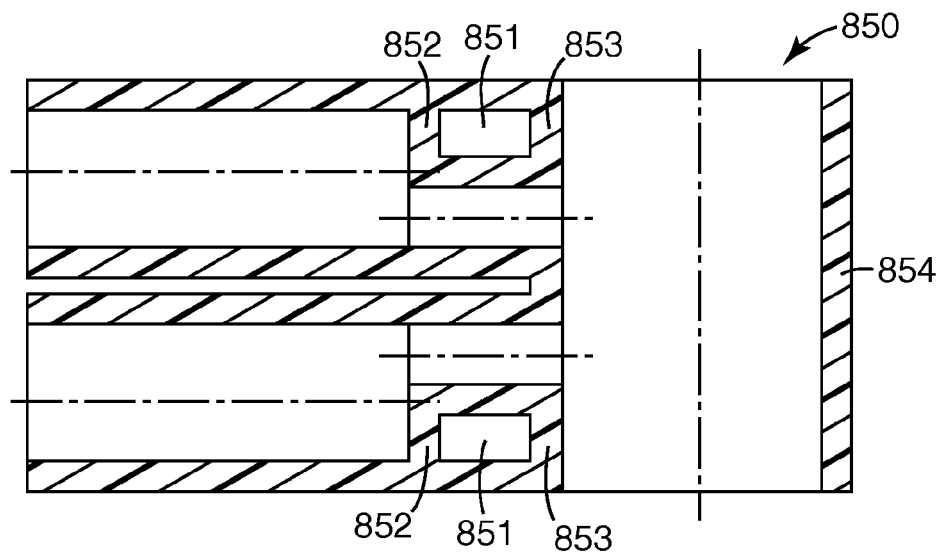
FIG. 22 is a schematic cross-sectional view of a capsule having two windows according to an embodiment of the invention.

FIG. 22 shows a cartridge 850 having windows 851. In this embodiment the front walls 852 of the cartridge chambers are separated from the wall 853 forming the bearing shell 854. Such an embodiment may also provide for reducing plastic material accumulation, better accuracy of the parts and an improved seal between a nozzle (not shown) and the cartridge 850.

Figure 23:
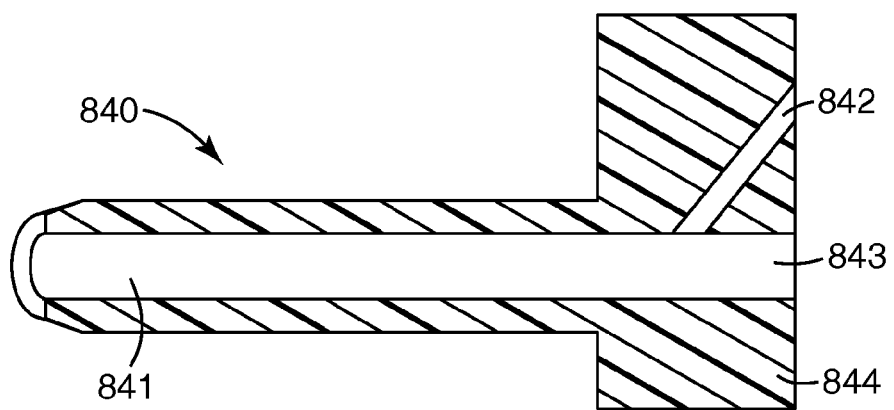
FIG. 23 is a schematic cross-sectional view of a nozzle having two separate inlets according to an embodiment of the invention.

FIG. 23 shows a nozzle 840 having a mixing channel 841 and inlets 842, 843. Inlet 843 may be, as shown, a continuation of the mixing channel 841 so that the mixing channel 841 as well as the inlet 843 may be molded by use of a single mold core. The inlet 842 is inclined with respect to the mixing channel 841 and merges with it inside of the nozzle 840. As can be seen the inlets 842, 843 form separate openings at the outer surface of the bearing member 844 of the nozzle 840. In contrast to having one large common inlet on the bearing member spanning two outlets of the cartridge, two smaller individual inlets on the bearing member directly connected to corresponding cartridge outlets provide a smaller overall cross-sectional area at the interface between the bearing member of the nozzle and the bearing shell of a cartridge (not shown). The pressure from material forced through the inlet (s), for example when material is dispensed from the capsule, therefore may have a reduced effect on forcing the bearing shell away from the bearing member, thus causing leakage. This is because the area of the bearing shell loaded by such material pressure is rather small. As an advantage the quality of the seal required between the cartridge and the nozzle may be less.

Figure 19B:
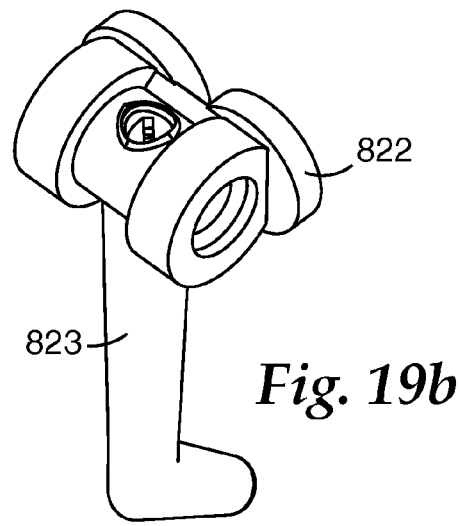
Figure 24:
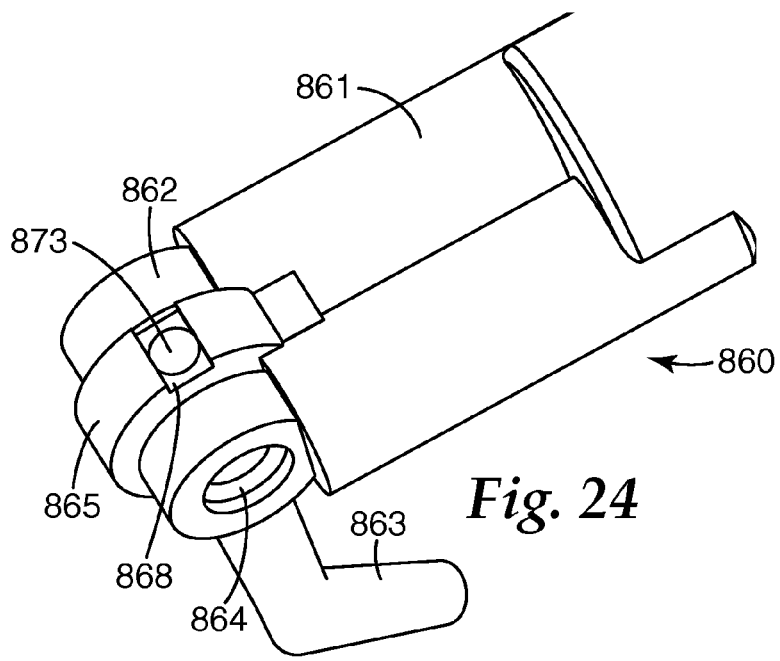
FIG. 24 is a perspective view of a capsule having a nozzle with a raised ridge for closing and opening of the capsule according to an embodiment of the invention.
Figure 25:
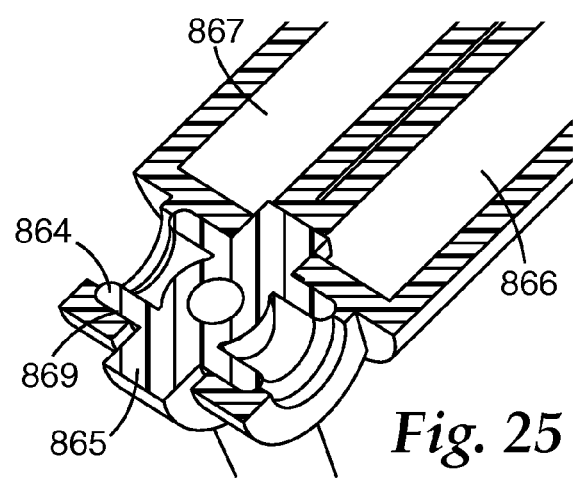
FIG. 25 is a cross-sectional perspective view of a capsule of FIG. 24.
Figure 26:
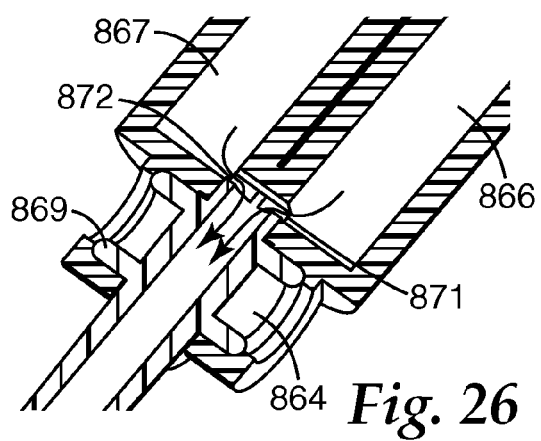
FIG. 26 is another cross-sectional perspective view of a capsule of FIG. 24.

FIGS. 24 through 26 show a capsule 860 with a nozzle 863. The nozzle 863 is movably held within a cartridge front 862. The nozzle 863 comprises a bearing member 864 that tightly seals with a bearing shell 869 (shown in FIG. 25) of the cartridge front. Further, the nozzle 863 has an annular ridge 865 protruding from the outer surface of the bearing member 864. In the storage position of the nozzle 863 the annular ridge 865 provides a part of the wall of the material chambers 866, 867 of the cartridge 861. Thus, apertures or outlets 871, 872 are formed in the chambers 866, 867 that are closed by surfaces of the annular ridge 865 (see FIG. 25). The annular ridge 865 has a groove 868 which upon pivoting of the nozzle from the storage position to the operating position is displaced to a position in which it is in fluid communication with the outlets 871, 872 (see FIG. 26). The groove is connected to a mixing channel 873 of the nozzle so that in the operative position of the nozzle a fluid pathway between the chambers 866, 867 and the mixing channel 873 is established. In other words the nozzle 863 forms in co-operation with the cartridge 861 a valve for closing and opening of the material chambers 866, 867. The groove may be at least partially surrounded by a raised ridge (not shown) which cooperates with the cartridge 861 and/or the bearing shell 869 to provide a seal for the pathway so that material forced towards the mixing channel follows the pathway without substantial leakage. The raised ridge may have a leading section and a trailing section as described for example for the embodiment shown in FIGS. 15a and 15b. An advantage of this embodiment is that the wall thicknesses of the plastic material surrounding the nozzle may be optimized so that inaccuracies that may arise from non-uniformly shrinking of molded material during cooling may be reduced. Further, a more efficient seal may be provided between the nozzle and the capsule. The embodiment shown may have a cartridge that is formed as one piece or the cartridge may be made of at least two parts as shown in FIGS. 19a, 19b and 20.

Figure 27A:
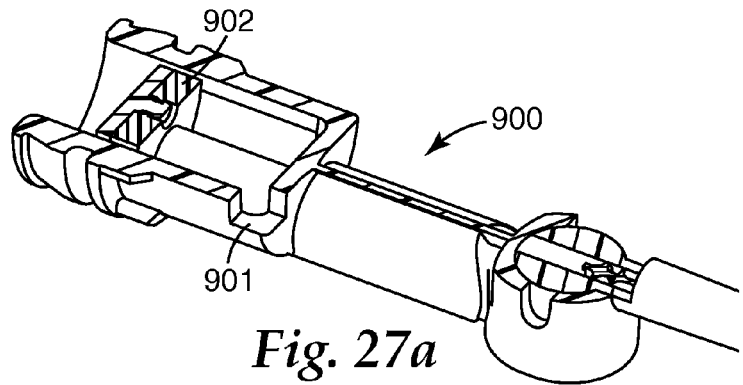
FIGS. 27a, 27b are cross-sectional perspective views of a capsule having an indicator according to an embodiment of the invention.
Figure 27B:
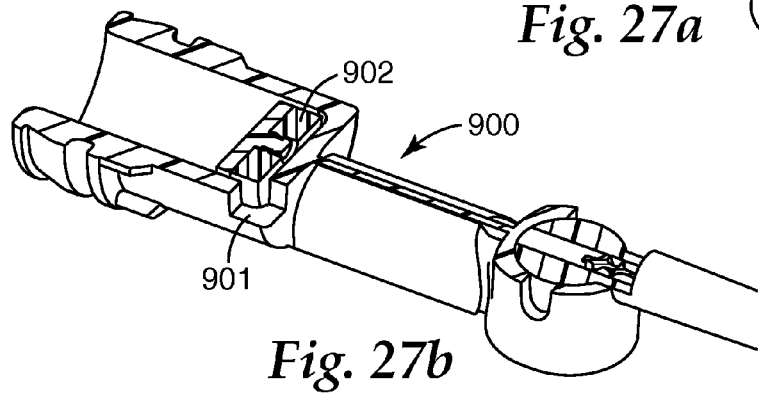

In FIGS. 27a, 27b a capsule is shown having a fill level indicator for indicating the fill level to a user. In the example shown in FIG. 27a the fill level indicator comprises a window 901 in the cartridge. Through the window 901 the piston 902 of the capsule becomes visible (FIG. 27b) as soon as the remaining material in the capsule is low. This may be advantageous for a user dispensing a material from especially an opaque capsule, because with such a feature he can recognize a low fill level early and control dispensation of the remaining material at a slower rate, for example, to avoid being surprised when the piston reaches its end position. Further, the user may initiate preparation of a second capsule when the fill level becomes low. For example, a dentist may have his assistant prepare a new capsule, when the fill level indicator of the capsule he is using shows that the material is almost gone.

Figure 28A:
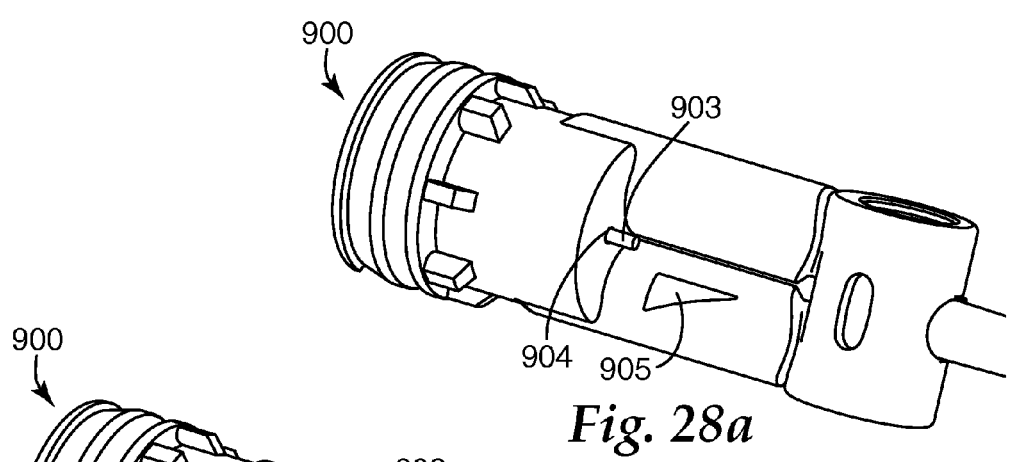
FIGS. 28a, 28b are cross-sectional perspective views of a capsule having an alternative indicator according to an embodiment of the invention.
Figure 28B:
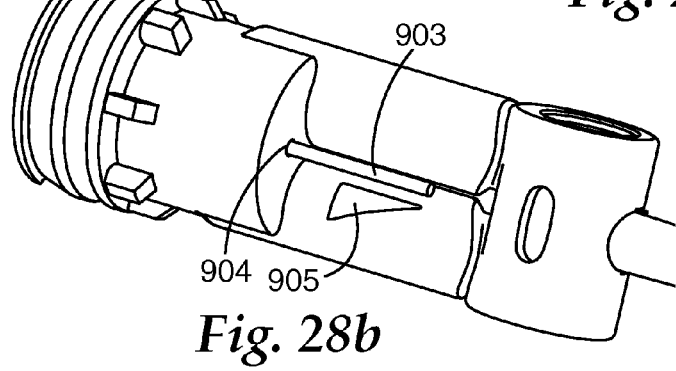

FIGS. 28a, 28b show an embodiment of a capsule 900 in which the fill level indicator comprises a window 904 and an indicator member 903. The indicator member 903 extends through the window 904 and may be visible already when the capsule is at its maximum fill level. During dispensation of material from the capsule the indicator member 903 moves so that a user can observe the fill level continuously. The capsule 900 may also comprise an indication, for example a scale, so that the user can determine the actual amount of paste left in the capsule. Alternatively the indicator member may be invisible initially and appear when the fill level of the capsule becomes low as described for the embodiment shown in FIGS. 27a, 27b.

Figure 29:
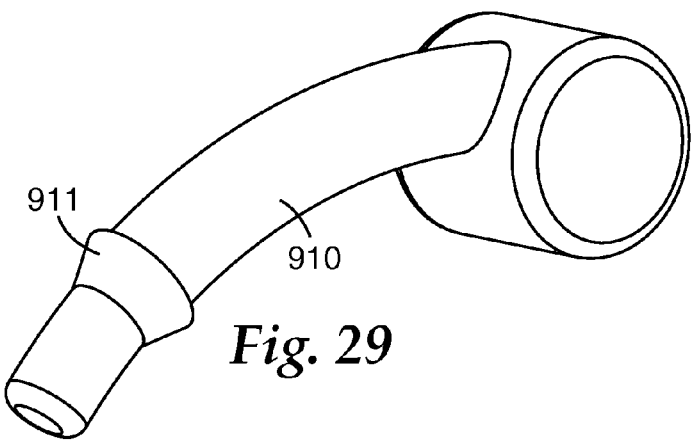
FIG. 29 is a perspective view of a nozzle having a retention rim according to an embodiment of the invention.

FIG. 29 shows a front portion of a nozzle 910 having a retention member 911 for engaging with a co-operative engaging member of an extension tip (not shown). Such a tip may have a reduced outer diameter relative to the diameter of the nozzle 910 so that a user can access certain places, for example like a root channel of a tooth.

Figure 30:
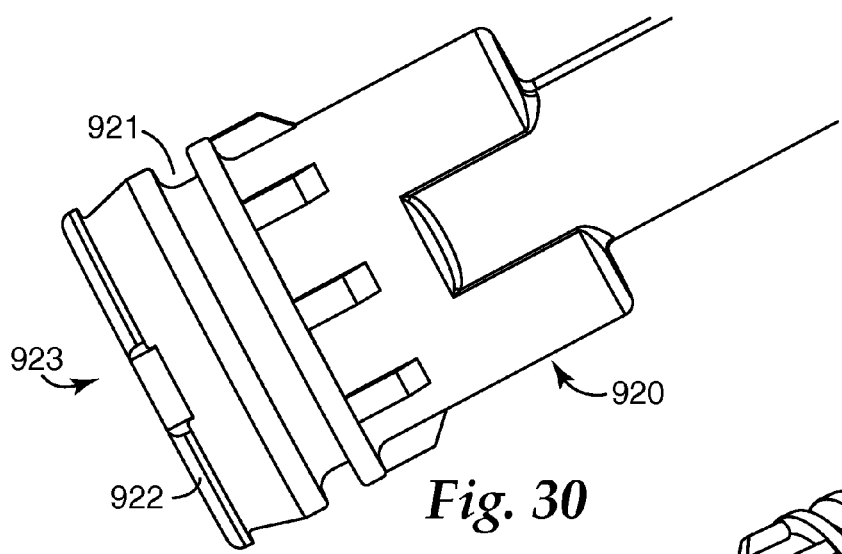
FIG. 30 is a perspective view of a capsule having a rim at the cartridge rear end according to an embodiment of the invention.

In FIG. 30 a capsule 920 is shown. The capsule 920 has a rim 922 adjacent the rear end 923 of the capsule and in front of the rim 922 an annular groove 921 for engagement with a dispensing applicator. It has been found that the annular rim 922 reinforces the part of the capsule behind the groove 921 and furthermore may provide a security stop preventing the capsule to separate from the applicator in case the capsule is overloaded by applying too high forces through the applicator.

Figure 31:
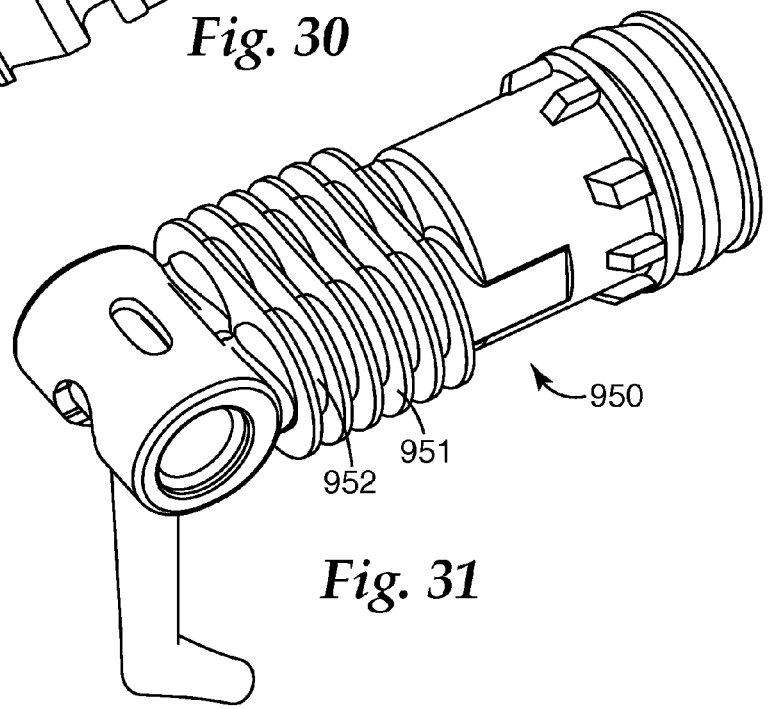
FIG. 31 is a perspective view of a capsule having reinforcement ribs according to an embodiment of the invention.

FIG. 31 shows an embodiment of a capsule 950 having reinforcement ribs 951 which reduce the elasticity of the cartridge walls 952. Such a design helps to provide good stability to the cartridge walls 952 that may be pressurized during dispensation of material from the capsule. Further the design provides for molding the cartridge walls 952 more accurately than just making the cartridge walls thicker. This is because a thick wall generally tends to inhomogeneously shrink when the molded material hardens, but thinner walls as implemented through the ribs 951 in this embodiment generally tend to more homogeneously shrink after molding. High accuracy is generally desirable because a piston used for extruding material from the capsule typically seals with the cartridge walls and variation of the cartridge wall thickness would eventually affect that seal.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. A capsule for storing and dispensing dental material, comprising
   a cartridge for the dental material; and
   a nozzle, the nozzle being pivotable with respect to the cartridge between a first position in which the capsule is closed for storage and a second position in which the capsule is opened for dispensing the dental material;
   wherein one of the nozzle and the cartridge comprises a bearing member and the other one of the nozzle and the cartridge comprises a bearing shell, the bearing member and bearing shell forming a pivot;
   wherein the bearing member has a non-circular cross-sectional shape that matches the non-circular shape of the bearing shell in the first position and upon pivoting the nozzle from the first position to the second position, the shape of the bearing member mismatches the shape of the bearing shell to improve the seal between the bearing member and the bearing shell relative to the first position.

2. The capsule of claim 1, wherein the seal is improved due to an increase in pressure between at least a part of the surface of the bearing member and a corresponding opposite part of the surface of the bearing shell in the second position of the nozzle compared to the first position.

3. The capsule of claim 1, wherein the nozzle comprises the bearing member and the cartridge comprises the bearing shell.

4. The capsule of claim 1, wherein the cartridge comprises a first chamber for containing a first material component, and a second chamber for containing a second material component, each chamber opening into an outlet.

5. The capsule of claim 4, comprising a plunger for dispensing material from the cartridge and through the nozzle, wherein the nozzle comprises a cannula comprising a passageway, and wherein the first position of the nozzle relative to the capsule is a storage position in which the nozzle closes off the at least one outlet of the cartridge, and wherein the second position is an operative position in which the passageway of the nozzle is in fluid communication with the outlet(s) of the cartridge, and wherein the nozzle comprises a static mixer within the cannula.

6. The capsule according to claim 4, wherein the bearing member comprises at least one blind hole aligned with and corresponding to the outlet(s) of the cartridge when the nozzle is positioned in first position.

7. The capsule of claim 1, wherein the nozzle comprises a mixing channel providing a first inlet into the mixing channel, and further, a second inlet merging with the mixing channel.

8. The capsule of claim 1, comprising a rim at the rear most end of the cartridge and a groove in a distance in front of the rim.

9. The capsule of claim 1, wherein the bearing member is made of a plastic material comprising at least one friction-reducing additive.

10. The capsule of claim 1, further comprising a locking mechanism to lock the nozzle in operative position, wherein the locking mechanism is formed by at least one detent provided at the bearing shell for engagement with the nozzle cannula.

11. The capsule according to claim 1, wherein the capsule is filled with a material selected from among a resin modified glass ionomer luting/filling/core build-up material, a resin based luting/filling/core build-up material, and temporary crown and bridge material.

12. The capsule according to claim 1, in combination with a handheld dispenser wherein the handheld dispenser pushes the material out of the capsule.

13. A method of manufacturing the capsule of claim 1, comprising the steps of molding the nozzle and subsequently molding the cartridge with the bearing shell around the bearing member.

14. A method of making the capsule of claim 1, wherein the method comprises the steps of providing the nozzle having the bearing member, and then injection molding the cartridge with the bearing shell around the bearing member.

* * * * *

UNITED STATES PATENT AND TRADEMARK OFFICE
CERTIFICATE OF CORRECTION

PATENT NO. : 8,328,553 B2  
APPLICATION NO. : 12/281996  
DATED : December 11, 2012  
INVENTOR(S) : Bruce Robert Broyles Page 1 of 1

It is certified that error appears in the above-identified patent and that said Letters Patent is hereby corrected as shown below:

In the Specification  
Column 1  
Line 59   Delete "Keta™" and insert -- Ketac™ --, therefor.

Column 2  
Line 56   Delete "scaling" and insert -- sealing --, therefor.

Column 4  
Line 60   Delete "scals" and insert -- seals --, therefor.

Column 6  
Line 2   Delete "Ultra" and insert -- E Ultra --, therefor.

Column 11  
Line 1   Delete "seating" and insert -- sealing --, therefor.

Column 12  
Line 21   Delete "invention:" and insert -- invention; --, therefor.  
Line 40   Delete "invention:" and insert -- invention; --, therefor.

Column 14  
Lines 4-5   Delete "in in" and insert -- in --, therefor.

Column 17  
Line 16   Delete "T his" and insert -- This --, therefor.

In the Claims  
Column 22  
Line 2   In Claim 12, delete "dispenser" and insert -- dispenser, --, therefor.

Signed and Sealed this  
Eleventh Day of June, 2013

Teresa Stanek Rea  
*Acting Director of the United States Patent and Trademark Office*